US009487834B2

(12) United States Patent
Held et al.

(10) Patent No.: US 9,487,834 B2
(45) Date of Patent: Nov. 8, 2016

(54) MAIZE EVENT HCEM485, COMPOSITIONS AND METHODS FOR DETECTING AND USE THEREOF

(71) Applicant: Stine Seed Farm, Inc., Adel, IA (US)

(72) Inventors: Bruce Held, Ames, IA (US); Harry Stine, Adel, IA (US); Vaithilingam Sekar, Adel, IA (US); Ryan E. Pesch, Jr., Ames, IA (US); Angela R. Umthun, Johnston, IA (US); Kelley S. Muir, Rippey, IA (US); Jason D. Behn, Johnston, IA (US); Herbert Martin Wilson, Durham, NC (US)

(73) Assignee: Stive Seed Farm, Adel, IA (US)

( * ) Notice: Subject to any disclaimer, the term of this patent is extended or adjusted under 35 U.S.C. 154(b) by 0 days.

(21) Appl. No.: 14/256,525

(22) Filed: Apr. 18, 2014

(65) Prior Publication Data

US 2016/0002742 A1 Jan. 7, 2016

Related U.S. Application Data

(62) Division of application No. 13/211,622, filed on Aug. 17, 2011, now Pat. No. 8,759,618.

(51) Int. Cl.

| | |
|---|---|
| ***C12Q 1/68*** | (2006.01) |
| ***C12P 19/34*** | (2006.01) |
| ***A01H 1/04*** | (2006.01) |
| ***A01H 5/10*** | (2006.01) |
| ***C12N 9/10*** | (2006.01) |
| ***C12N 15/82*** | (2006.01) |

(52) U.S. Cl.

CPC ............... *C12Q 1/6895* (2013.01); *A01H 1/04* (2013.01); *A01H 5/10* (2013.01); *C12N 9/1092* (2013.01); *C12N 15/8275* (2013.01); *C12Y 205/01019* (2013.01); *C12Q 2600/13* (2013.01)

(58) Field of Classification Search

USPC ................................................ 435/6.12, 91.2

See application file for complete search history.

(56) References Cited

U.S. PATENT DOCUMENTS

| | | | |
|---|---|---|---|
| 4,535,060 | A | 8/1985 | Comai |
| 4,769,061 | A | 9/1988 | Comai |
| 5,094,945 | A | 3/1992 | Comai |
| 5,304,712 | A | 4/1994 | Harper, II |
| 5,310,667 | A | 5/1994 | Eichholtz |
| 5,633,435 | A | 5/1997 | Barry |
| 5,866,775 | A | 2/1999 | Eichholtz |
| 6,040,497 | A | 3/2000 | Spencer |
| 6,225,114 | B1 | 5/2001 | Eichholtz |
| 6,566,587 | B1 | 5/2003 | Lebrun |
| 7,045,684 | B1 | 5/2006 | Held |
| 7,626,077 | B2 | 12/2009 | Held |
| 7,632,985 | B2 | 12/2009 | Malven |
| 7,807,791 | B2 | 10/2010 | Sekar |
| 7,928,296 | B2 | 4/2011 | Chicoine |
| 7,951,995 | B2 | 5/2011 | Guida, Jr. et al. |

OTHER PUBLICATIONS

Rychlik et al., Nucleic Acids Research 17(21), 8543-8551 (1989).*

Stine Seed Farm: "Request for extension of determination of nonregulated status to the additional regulated article: Maize line HCEM485" Mar. 2, 2009, XP002686269, Retrieved from the internet: www.aphis.usda.gov/foia/foia_requests/2011/Biotechnology%20and%20Regulatory%20Services%20(BRS)/10-594%20-%20%20Copy%20of%20Petition%2009-063-01p/10-594%20Records.pdf.

Herouet-Guicheney et al. "Safety evaluation of the double mutant 5-enolypyruvylshikimate-3-phosphate synthase (2mEPSPS) from maize that confers tolerance to glyphosate herbicide in transgenic plants" Regulatory toxicology and Pharmacology, vol. 54 No. 2, pp. 143-153 (2009).

Syngenta Seeds S.A.S.: "Event-specific method for the quantification of maize line GA21 using real time PCR" Mar. 30, 2010, XP002686271, retrieved from the internet: http://gmo-crl.jrc.ec.europa.eu/summaries/GA21Syngenta_validated_Method_correctedVersion1.pdf.

Monsanto Biotechnology Regulatory Sciences: "Event-specific method for the quantification of maize line GA21 using real time PCR" Jan. 17, 2005, XP00268272, retried from the internet: http://gmo-crl.jrc.ec.europa.eu/summaries/GA21-WEB-Protocol%20Validation.pdf.

PCT search and Invitation PCT/US2012/049855, Nov. 13, 2012 and written opinion Jan. 30, 2013.

GenBank X63374.1 Apr. 18, 2005.

* cited by examiner

*Primary Examiner* — Kenneth Horlick

(74) *Attorney, Agent, or Firm* — Patricia A. Sweeney

(57) ABSTRACT

Maize event HCEM485 is provided, in which plants comprising the event are tolerant to exposure to a glyphosate herbicide. Maize genomic polynucleotides flanking the insert DNA providing glyphosate tolerance are provided. The plant or part thereof having the event comprises a junction region of the insert DNA and maize plant genomic sequences. Methods and primers and probes to detect the presence of the event are provided, as well as kits which employ such primers and probes.

10 Claims, 5 Drawing Sheets

ATGTTACTATGGTGCCTTCTTATCCCACTGAGCATTGGTATATTTAGAGGTTTTTGTT
GAACATGCCTAAATCATCTCAATCAACGATGGACAATCTTTTCTTCGATTGAGCTGA
GGTACGTCATCTACAGGATAGGACCTTGAGAATATGTGTCCGTCAATAGCTAACCCT
CTACTAATTTTTTCAATCAAGCAACCTATTGGCTTGACTTTAATTCGTACCGGCTTCT
ACTACTTCTACAGTATTTTGTCTCTATAAATTGCAGCTACAACAGTCAGAACGGCTG
GCTTTAAAATCAAATGGCCTAAGGATCATTGAAAGGCATCTTAGCAATGTCTAAAAT
TATTACCTTCTCTAGACGTTGA*TG*TCTTATAGGGCTTGGACATGACACAGACATAAT
TTATATAGTATTAGATTGAGTGAGACTGGGTGGGTTTAAATTCCAAGCAAGTCAAAC
TTGTTCTTAATTTTTTCCAATCCCATTCAATCCATGGGTAACGGGATTAACCGAACAA
TGTCTTATAGGGCTTGGACATGACACAGACATAATTTATATAGTATTAGTGCCGGTA
CCACACGGGTCTAATGTCGTGTTTAGGCCTCCATCCGGCATGATGATTGGCATAAGC
ACGACATGATTAGGTGGTCGACACGATTAAGCACGGCTTAAACCAGCTAGTAGTAT
GTAGATGTGATTGTGATATGTATATGTGATTGTGAATTGTGATTTATTATGGTTTTAA
GTATAATCAATTTACTTTATAATGGTATAAATGTTTAAATTCTAAAACTGTATATATA
ATTTTAAAGATTTTCTATAATTCTAGACTGACACAAATACTATTAGTTGTTAATGTTA
TATAGTGCCGGTATGATACAATTAAATATTATAGTGTAGTGTCTAGATCTACACTAG
TGCCGACACGACACAATATAATTAGTAATAGTGCTTAATAATACTTAGTGTACCTA
CTGGGCGGTTCGTCTGGCTATCTATAATCATGAATACTCGTGTGCTCGTCACCGGTC
ACGGCCAGGAGATATGACGACGGCTGTTGTTTTCTTCTGGCGTGGGGCTGCGCGAAG
GGATAagaAGgcAccatagtAaCAt

Figure 4

SEQUENCE LISTING

```
<160> NUMBER OF SEQ ID NOS: 22

<210> SEQ ID NO 1
<211> LENGTH: 6010
<212> TYPE: DNA
<213> ORGANISM: Zea Mays

<400> SEQUENCE: 1

atcgattgca accttcaaat tctcttcgat cttccttcca aattcatcta atatttcatc     60

ctcggcaagg aaatcttcta acgtgtaaac ttcactggga tccaactcga aaggatcaaa    120

ctctccctct ggttcgtttg acattgtgga tggagtgact aacctgctaa caccctgcaa    180

caatttatac aggagcatat cctcatgcac acgcaaaact gatgttgtcc acaagacacg    240

cacaggacac gcacaggaca cgcaaacagt ttcagactca tgcacacgca catcagtttc    300

agactcaggc acacgcacat caaatcacct tcgcttgtcg atgagtcgca gccgcatcgt    360

acaatggcga ttttaccgac gataaggcat gggagcacga gccgtcgccg tcgccttgcg    420

agacgacggg agcgatctct cccttcattt aatctcttcc acgtcaggtt attttgctga    480

gatggcagta tacagacggc aaagttaatg ccgttgtaca tgcccttaga ctcttccgtc    540

accaactcac ttagattttt acaacggaac ataaggttcg cttgcagact tacatataag    600

gtatagttgc ataataatcg ccttatgctg tacattgcga cacccgtaaa tattcgatga    660

aatattagta cacaatatta aataagaacg aacaatacat atattatcat tgatcttagt    720

atctcctttt gctcctcgta gaacaattct gtgtaaatta tgcgtaaaat tcgaggacca    780

aaacattggc tagaaaaata cctaaaatca gttttgcaat tgtttctgat tttcctcata    840

ttttcttgct tataaagttt tccaaaagta ccattttgga tgaaaaaacg gaaaacaacg    900

ctggtctact tgtaaatttg gtagtgacat ttgggaccgt ctagacacga cctaaaaata    960

gtagtctaaa acatagtctg acacgatgcc ttaaaaatag acgacaaagc acaacacgat   1020

tagatgtgtc gtgttttgac cgacacgaca caaagtaagg cacgatttaa aacccaataa   1080

ataatatttt aatggttatt ttatgttcca ataattttca tctcttcaaa aaaatgttat   1140

agaaatcatt gatacttagt tgaatatcct aacacaatat atatatatat attaatatat   1200

atatatatca attttaagtc actttgctag acatagtaat atattttaaa tattttctct   1260

ttcttgtata tttttaaaat acacatcagt ttttatatgt gtcgtgcttg aaccgacacg   1320

atataatcat cggttcgccg tacttctaga tcatgatgtt cctaggtttt aatattaaga   1380

gacggtctat attaactcaa aactatttcg tgaaaggcta actcgaaaaa aaaatgaatg   1440

taatcacggc ccgtcctgga ttcgagattc taacgtttca ttcgtgtcca gtgtgcacac   1500

ttgtggaaaa ggaagacgaa gaaaaaaacc aacaactaac tccggcccgc cggatgcgcc   1560

cacctacttc cccctcgccc ctctcatggt ctctctcgcg cccagatctg ctactagacg   1620

gcaccgctgc agcgcgtcgt gtcgcggggg ttggtggcag gcagcgagag cttgccgttc   1680

ctctctctca gttgtcaggt cctaggctca cctcaccggc tcccagcccg cttctatttc   1740
```

-continued

```
ttcctccccg accccgtgca ggtggcagtc cagtccacgc caccaaccgc gaggcgaacc   1800
aaaccaaccc actctcccca accccgcgcg cccaggccgc ccgccctacc aaccatcggc   1860
gtcggcaatg gcggccatgg cgaccaaggc cgccgcgggc accgtgtcgc tggacctcgc   1920
cgcgccgtcg cgccgccacc accgcccgag ctcggcgcgc ccgcccgccc gccccgccgt   1980
ccgcgggctg cgggcgcctg ggcgccgcgt gatcgccgcg ccgccggcgg cggcagcggc   2040
ggcggcggtg caggcgggtg ccgaggagat cgtgctgcag cccatcaagg agatctccgg   2100
caccgtcaag ctgccggggt ccaagtcgct ttccaaccgg atcctcctgc tcgccgccct   2160
gtccgaggtg agcgattttg gtgcttgctg cgctgccctg tctcactgct acctaaatgt   2220
tttgcctgtc gaataccatg gattctcggt gtaatccatc tcacgatcag atgcaccgca   2280
tgtcgcatgc ctagctctct ctaatttgtc tagtagtttg tatacggatt aatattgata   2340
aatcggtacc gcaaaagcta ggtgtaaata aacactagaa aattggatgt tcccctatcg   2400
gcctgtactc ggctactcgt tcttgtgatg gcatgctgtc tcttcttggt gtttggtgaa   2460
caaccttatg aaatttgggc gcaaagaact cgccctcaag ggttgatctt atgccatcgt   2520
catgataaac agtggagcac ggacgatcct ttacgttgtt tttaacaaac tttgtcagaa   2580
aactagcatc attaacttct taatgacgat ttcacaacaa aaaaaggtaa cctcgctact   2640
aacataacaa aatacttgtt gcttattaat tatatgtttt ttaatctttg atcaggggac   2700
aacagtggtt gataacctgt tgaacagtga ggatgtccac tacatgctcg gggccttgag   2760
gactcttggt ctctctgtcg aagcggacaa agctgccaaa agagctgtag ttgttggctg   2820
tggtggaaag ttcccagttg aggattctaa agaggaagtg cagctcttct tggggaatgc   2880
tggaactgca atgcggccat tgacagcagc tgttactgct gctggtggaa atgcaacgta   2940
tgtttcctct ctttctctct acaatacttg ctggagttag tatgaaaccc atgggtatgt   3000
ctagtggctt atggtgtatt ggtttttgaa cttcagttac gtgcttgatg gagtaccaag   3060
aatgagggag agacccattg gcgacttggt tgtcggattg aagcagcttg gtgcagatgt   3120
tgattgtttc cttggcactg actgcccacc tgttcgtgtc aatggaatcg gagggctacc   3180
tggtggcaag gttagctact aagggccaca tgttacattc ttctgtaaat ggtacaacta   3240
ttgtcgagct tttgcatttg taaggaaagc attgattgat ctgaatttga tgctacacca   3300
caaaatatcc tacaaatggt catccctaac tagcaaacaa tgaagtaata cttggcatgt   3360
gtttatcaaa ttaatttcca tcttctgggg cattgcctgt tttctagtct aatagcattt   3420
gtttttagca ttaattagct cttacaattg ttatgttcta caggtcaagc tgtctggctc   3480
catcagcagt cagtacttga gtgccttgct gatggctgct cctttggctc ttggggatgt   3540
ggagattgaa atcattgata aattaatctc cattccctac gtcgaaatga cattgagatt   3600
gatggagcgt tttggtgtga aagcagagca ttctgatagc tgggacagat tctacattaa   3660
gggaggtcaa aaatacaagt aagctctgta atgtatttca ctactttgat gccaatgttt   3720
cagttttcag ttttccaaac agtcgcatca atatttgaat agatgcactg tagaaaaaaa   3780
atcattgcag ggaaaaacta gtactgagta ttttgactgt aaattatttt accagtcgga   3840
atatagtcag tctattggag tcaagagcgt gaaccgaaat agccagttaa ttatcccatt   3900
atacagagga caaccatgta tactattgaa acttggttta taagagaatc taggtagctg   3960
gactcgtagc tgcttggcat ggataccttc ttatctttag gaaaagacac ttgatttttt   4020
ttttctgtgg ccctctatga tgtgtgaacc tgcttctcta ttgctttaga aggatatatc   4080
```

-continued

```
tatgtcgtta tgcaacatgc ttcccttagc catttgtact gaaatcagtt tcataagttc   4140

gttagtggtt ccctaaacga aaccttgttt ttctttgcaa tcaacaggtc ccctaaaaat   4200

gcctatgttg aaggtgatgc ctcaagcgca agctatttct tggctggtgc tgcaattact   4260

ggagggactg tgactgtgga aggttgtggc accaccagtt tgcaggtaaa gatttcttgg   4320

ctggtgctac aataactgct tttgtctttt tggtttcagc attgttctca gagtcactaa   4380

ataacattat catctgcaaa tgtcaaatag acatacttag gtgaattcat gtaaccgttt   4440

ccttacaaat ttgctgaaac ctcagggtga tgtgaagttt gctgaggtac tggagatgat   4500

gggagcgaag gttacatgga ccgagactag cgtaactgtt actggcccac cgcgggagcc   4560

atttgggagg aaacacctca aggcgattga tgtcaacatg aacaagatgc ctgatgtcgc   4620

catgactctt gctgtggttg ccctctttgc cgatggcccg acagccatca gagacggtaa   4680

aacattctca gccctacaac catgcctctt ctacatcact acttgacaag actaaaaact   4740

attggctcgt tggcagtggc ttcctggaga gtaaaggaga ccgagaggat ggttgcgatc   4800

cggacggagc taaccaaggt aaggctacat acttcacatg tctcacgtcg tctttccata   4860

gctcgctgcc tcttagcggc ttgcctgcgg tcgctccatc ctcggttgct gtctgtgttt   4920

tccacagctg ggagcatctg ttgaggaagg gccggactac tgcatcatca cgccgccgga   4980

gaagctgaac gtgacggcga tcgacacgta cgacgaccac aggatggcca tggccttctc   5040

ccttgccgcc tgtgccgagg tccccgtgac catccgggac cctgggtgca cccggaagac   5100

cttccccgac tacttcgatg tgctgagcac tttcgtcaag aattaataaa gcgtgcgata   5160

ctaccacgca gcttgattga agtgataggc ttgtgctgag gaaatacatt tcttttgttc   5220

tgttttttct ctttcacggg attaagtttt gagtctgtaa cgttagttgt ttgtagcaag   5280

tttctatttc ggatcttaag tttgtgcact gtaagccaaa tttcatttca agagtggttc   5340

gttggaataa taagaataat aaattacgtt tcagtggctg tcaagcctgc tgctacgttt   5400

taggagatgg cattagacat tcatcatcaa caacaataaa accttttagc ctcaaacaat   5460

aatagtgaag ttattttttta gtcctaaaca agttgcatta ggatatagtt aaaacacaaa   5520

agaagctaaa gttagggttt agacatgtgg atattgtttt ccatgtatag tatgttcttt   5580

ctttgagtct catttaacta cctctacaca taccaacttt agtttttttt ctacctcttc   5640

atgttactat ggtgccttct tatcccactg agcattggta tatttagagg tttttgttga   5700

acatgcctaa atcatctcaa tcaacgatgg acaatctttt cttcgattga gctgaggtac   5760

gtcatctaca ggataggacc ttgagaatat gtgtccgtca atagctaacc ctctactaat   5820

tttttcaatc aagcaaccta ttggcttgac tttaattcgt accggcttct actacttcta   5880

cagtattttg tctctataaa ttgcagctac aacagtcaga acggctggct ttaaaatcaa   5940

atggcctaag gatcattgaa aggcatctta gcaatgtcta aaattattac cttctctaga   6000

cgttgatatc                                                          6010
```

<210> SEQ ID NO 2
<211> LENGTH: 6010
<212> TYPE: DNA
<213> ORGANISM: Zea mays

<400> SEQUENCE: 2

```
atcgattgca accttcaaat tctcttcgat cttccttcca aattcatcta atatttcatc     60

ctcggcaagg aaatcttcta acgtgtaaac ttcactggga tccaactcga aaggatcaaa    120

ctctccctct ggttcgtttg acattgtgga tggagtgact aacctgctaa caccctgcaa    180
```

-continued caatttatac aggagcatat cctcatgcac acgcaaaact gatgttgtcc acaagacacg 240
cacaggacac gcacaggaca cgcaaacagt ttcagactca tgcacacgca catcagtttc 300
agactcaggc acacgcacat caaatcacct tcgcttgtcg atgagtcgca gccgcatcgt 360
acaatggcga ttttaccgac gataaggcat gggagcacga gccgtcgccg tcgccttgcg 420
agacgacggg agcgatctct cccttcattt aatctcttcc acgtcaggtt attttgctga 480
gatggcagta tacagacggc aaagttaatg ccgttgtaca tgcccttaga ctcttccgtc 540
accaactcac ttagattttt acaacggaac ataaggttcg cttgcagact tacatataag 600
gtatagttgc ataataatcg ccttatgctg tacattgcga cacccgtaaa tattcgatga 660
aatattagta cacaatatta aataagaacg aacaatacat atattatcat tgatcttagt 720
atctcctttt gctcctcgta gaacaattct gtgtaaatta tgcgtaaaat tcgaggacca 780
aaacattggc tagaaaaata cctaaaatca gttttgcaat tgtttctgat tttcctcata 840
ttttcttgct tataaagttt tccaaaagta ccattttgga tgaaaaaacg gaaaacaacg 900
ctggtctact tgtaaatttg gtagtgacat ttgggaccgt ctagacacga cctaaaaata 960
gtagtctaaa acatagtctg acacgatgcc ttaaaaatag acgacaaagc acaacacgat 1020
tagatgtgtc gtgttttgac cgacacgaca caaagtaagg cacgatttaa aacccaataa 1080
ataatatttt aatggttatt ttatgttcca ataattttca tctcttcaaa aaaatgttat 1140
agaaatcatt gatacttagt tgaatatcct aacacaatat atatatatat attaatatat 1200
atatatatca attttaagtc actttgctag acatagtaat atattttaaa tattttctct 1260
ttcttgtata tttttaaaat acacatcagt ttttatatgt gtcgtgcttg aaccgacacg 1320
atataatcat cggttcgccg tacttctaga tcatgatgtt cctaggtttt aatattaaga 1380
gacggtctat attaactcaa aactatttcg tgaaaggcta actcgaaaaa aaaatgaatg 1440
taatcacggc ccgtcctgga ttcgagattc taacgtttca ttcgtgtcca gtgtgcacac 1500
ttgtggaaaa ggaagacgaa gaaaaaaacc aacaactaac tccggcccgc cggatgcgcc 1560
cacctacttc cccctcgccc ctctcatggt ctctctcgcg cccagatctg ctactagacg 1620
gcaccgctgc agcgcgtcgt gtcgcggggg ttggtggcag gcagcgagag cttgccgttc 1680
ctctctctca gttgtcaggt cctaggctca cctcaccggc tcccagcccg cttctatttc 1740
ttcctccccg accccgtgca ggtggcagtc cagtccacgc caccaaccgc gaggcgaacc 1800
aaaccaaccc actctcccca accccgcgcg cccaggccgc ccgccctacc aaccatcggc 1860
gtcggcaatg gcggccatgg cgaccaaggc cgccgcgggc accgtgtcgc tggacctcgc 1920
cgcgccgtcg cgccgccacc accgcccgag ctcggcgcgc ccgcccgccc gccccgccgt 1980
ccgcgggctg cgggcgcctg ggcgccgcgt gatcgccgcg ccgccggcgg cggcagcggc 2040
ggcggcggtg caggcgggtg ccgaggagat cgtgctgcag cccatcaagg agatctccgg 2100
caccgtcaag ctgccggggt ccaagtcgct ttccaaccgg atcctcctgc tcgccgccct 2160
gtccgaggtg agcgattttg gtgcttgctg cgctgccctg tctcactgct acctaaatgt 2220
tttgcctgtc gaataccatg gattctcggt gtaatccatc tcacgatcag atgcaccgca 2280
tgtcgcatgc ctagctctct ctaatttgtc tagtagtttg tatacggatt aatattgata 2340
aatcggtacc gcaaaagcta ggtgtaaata aacactagaa aattggatgt tcccctatcg 2400
gcctgtactc ggctactcgt tcttgtgatg gcatgctgtc tcttcttggt gtttggtgaa 2460
caaccttatg aaatttgggc gcaaagaact cgccctcaag ggttgatctt atgccatcgt 2520

-continued

```
catgataaac agtggagcac ggacgatcct ttacgttgtt tttaacaaac tttgtcagaa   2580
aactagcatc attaacttct taatgacgat ttcacaacaa aaaaaggtaa cctcgctact   2640
aacataacaa aatacttgtt gcttattaat tatatgtttt ttaatctttg atcaggggac   2700
aacagtggtt gataacctgt tgaacagtga ggatgtccac tacatgctcg gggccttgag   2760
gactcttggt ctctctgtcg aagcggacaa agctgccaaa agagctgtag ttgttggctg   2820
tggtggaaag ttcccagttg aggattctaa agaggaagtg cagctcttct tggggaatgc   2880
tggaattgca atgcggtcat tgacagcagc tgttactgct gctggtggaa atgcaacgta   2940
tgtttcctct ctttctctct acaatacttg ctggagttag tatgaaaccc atgggtatgt   3000
ctagtggctt atggtgtatt ggtttttgaa cttcagttac gtgcttgatg gagtaccaag   3060
aatgagggag agacccattg gcgacttggt tgtcggattg aagcagcttg gtgcagatgt   3120
tgattgtttc cttggcactg actgcccacc tgttcgtgtc aatggaatcg gagggctacc   3180
tggtggcaag gttagctact aagggccaca tgttacattc ttctgtaaat ggtacaacta   3240
ttgtcgagct tttgcatttg taaggaaagc attgattgat ctgaatttga tgctacacca   3300
caaaatatcc tacaaatggt catccctaac tagcaaacaa tgaagtaata cttggcatgt   3360
gtttatcaaa ttaatttcca tcttctgggg cattgcctgt tttctagtct aatagcattt   3420
gtttttagca ttaattagct cttacaattg ttatgttcta caggtcaagc tgtctggctc   3480
catcagcagt cagtacttga gtgccttgct gatggctgct cctttggctc ttggggatgt   3540
ggagattgaa atcattgata aattaatctc cattccctac gtcgaaatga cattgagatt   3600
gatggagcgt tttggtgtga aagcagagca ttctgatagc tgggacagat tctacattaa   3660
gggaggtcaa aaatacaagt aagctctgta atgtatttca ctactttgat gccaatgttt   3720
cagttttcag ttttccaaac agtcgcatca atatttgaat agatgcactg tagaaaaaaa   3780
atcattgcag ggaaaaacta gtactgagta ttttgactgt aaattatttt accagtcgga   3840
atatagtcag tctattggag tcaagagcgt gaaccgaaat agccagttaa ttatcccatt   3900
atacagagga caaccatgta tactattgaa acttggttta taagagaatc taggtagctg   3960
gactcgtagc tgcttggcat ggataccttc ttatctttag gaaaagacac ttgatttttt   4020
ttttctgtgg ccctctatga tgtgtgaacc tgcttctcta ttgctttaga aggatatatc   4080
tatgtcgtta tgcaacatgc ttcccttagc catttgtact gaaatcagtt tcataagttc   4140
gttagtggtt ccctaaacga aaccttgttt ttctttgcaa tcaacaggtc ccctaaaaat   4200
gcctatgttg aaggtgatgc ctcaagcgca agctatttct tggctggtgc tgcaattact   4260
ggagggactg tgactgtgga aggttgtggc accaccagtt tgcaggtaaa gatttcttgg   4320
ctggtgctac aataactgct tttgtctttt tggtttcagc attgttctca gagtcactaa   4380
ataacattat catctgcaaa tgtcaaatag acatacttag gtgaattcat gtaaccgttt   4440
ccttacaaat ttgctgaaac ctcagggtga tgtgaagttt gctgaggtac tggagatgat   4500
gggagcgaag gttacatgga ccgagactag cgtaactgtt actggcccac cgcgggagcc   4560
atttgggagg aaacacctca aggcgattga tgtcaacatg aacaagatgc ctgatgtcgc   4620
catgactctt gctgtggttg ccctctttgc cgatggcccg acagccatca gagacggtaa   4680
aacattctca gccctacaac catgcctctt ctacatcact acttgacaag actaaaaact   4740
attggctcgt tggcagtggc ttcctggaga gtaaaggaga ccgagaggat ggttgcgatc   4800
cggacggagc taaccaaggt aaggctacat acttcacatg tctcacgtcg tctttccata   4860
gctcgctgcc tcttagcggc ttgcctgcgg tcgctccatc ctcggttgct gtctgtgttt   4920
```

-continued tccacagctg ggagcatctg ttgaggaagg gccggactac tgcatcatca cgccgccgga 4980
gaagctgaac gtgacggcga tcgacacgta cgacgaccac aggatggcca tggccttctc 5040
ccttgccgcc tgtgccgagg tccccgtgac catccgggac cctgggtgca cccggaagac 5100
cttccccgac tacttcgatg tgctgagcac tttcgtcaag aattaataaa gcgtgcgata 5160
ctaccacgca gcttgattga agtgataggc ttgtgctgag gaaatacatt tcttttgttc 5220
tgttttttct ctttcacggg attaagtttt gagtctgtaa cgttagttgt ttgtagcaag 5280
tttctatttc ggatcttaag tttgtgcact gtaagccaaa tttcatttca agagtggttc 5340
gttggaataa taagaataat aaattacgtt tcagtggctg tcaagcctgc tgctacgttt 5400
taggagatgg cattagacat tcatcatcaa caacaataaa accttttagc ctcaaacaat 5460
aatagtgaag ttattttttta gtcctaaaca agttgcatta ggatatagtt aaaacacaaa 5520
agaagctaaa gttagggttt agacatgtgg atattgtttt ccatgtatag tatgttcttt 5580
ctttgagtct catttaacta cctctacaca taccaacttt agtttttttt ctacctcttc 5640
atgttactat ggtgccttct tatcccactg agcattggta tatttagagg tttttgttga 5700
acatgcctaa atcatctcaa tcaacgatgg acaatctttt cttcgattga gctgaggtac 5760
gtcatctaca ggataggacc ttgagaatat gtgtccgtca atagctaacc ctctactaat 5820
tttttcaatc aagcaaccta ttggcttgac tttaattcgt accggcttct actacttcta 5880
cagtattttg tctctataaa ttgcagctac aacagtcaga acggctggct ttaaaatcaa 5940
atggcctaag gatcattgaa aggcatctta gcaatgtcta aaattattac cttctctaga 6000
cgttgatatc 6010

<210> SEQ ID NO 3
<211> LENGTH: 506
<212> TYPE: PRT
<213> ORGANISM: Zea mays

<400> SEQUENCE: 3

Met Ala Ala Met Ala Thr Lys Ala Ala Ala Gly Thr Val Ser Leu Asp
1 5 10 15

Leu Ala Ala Pro Ser Arg Arg His His Arg Pro Ser Ser Ala Arg Pro
20 25 30

Pro Ala Arg Pro Ala Val Arg Gly Leu Arg Ala Pro Gly Arg Arg Val
35 40 45

Ile Ala Ala Pro Pro Ala Ala Ala Ala Ala Ala Ala Val Gln Ala Gly
50 55 60

Ala Glu Glu Ile Val Leu Gln Pro Ile Lys Glu Ile Ser Gly Thr Val
65 70 75 80

Lys Leu Pro Gly Ser Lys Ser Leu Ser Asn Arg Ile Leu Leu Leu Ala
85 90 95

Ala Leu Ser Glu Gly Thr Thr Val Val Asp Asn Leu Leu Asn Ser Glu
100 105 110

Asp Val His Tyr Met Leu Gly Ala Leu Arg Thr Leu Gly Leu Ser Val
115 120 125

Glu Ala Asp Lys Ala Ala Lys Arg Ala Val Val Val Gly Cys Gly Gly
130 135 140

Lys Phe Pro Val Glu Asp Ser Lys Glu Glu Val Gln Leu Phe Leu Gly
145 150 155 160

Asn Ala Gly Ile Ala Met Arg Ser Leu Thr Ala Ala Val Thr Ala Ala
165 170 175

-continued

```
Gly Gly Asn Ala Thr Tyr Val Leu Asp Gly Val Pro Arg Met Arg Glu
            180                 185                 190

Arg Pro Ile Gly Asp Leu Val Val Gly Leu Lys Gln Leu Gly Ala Asp
        195                 200                 205

Val Asp Cys Phe Leu Gly Thr Asp Cys Pro Pro Val Arg Val Asn Gly
    210                 215                 220

Ile Gly Gly Leu Pro Gly Gly Lys Val Lys Leu Ser Gly Ser Ile Ser
225                 230                 235                 240

Ser Gln Tyr Leu Ser Ala Leu Leu Met Ala Ala Pro Leu Ala Leu Gly
                245                 250                 255

Asp Val Glu Ile Glu Ile Ile Asp Lys Leu Ile Ser Ile Pro Tyr Val
            260                 265                 270

Glu Met Thr Leu Arg Leu Met Glu Arg Phe Gly Val Lys Ala Glu His
        275                 280                 285

Ser Asp Ser Trp Asp Arg Phe Tyr Ile Lys Gly Gly Gln Lys Tyr Lys
    290                 295                 300

Ser Pro Lys Asn Ala Tyr Val Glu Gly Asp Ala Ser Ser Ala Ser Tyr
305                 310                 315                 320

Phe Leu Ala Gly Ala Ala Ile Thr Gly Gly Thr Val Thr Val Glu Gly
                325                 330                 335

Cys Gly Thr Thr Ser Leu Gln Gly Asp Val Lys Phe Ala Glu Val Leu
            340                 345                 350

Glu Met Met Gly Ala Lys Val Thr Trp Thr Glu Thr Ser Val Thr Val
        355                 360                 365

Thr Gly Pro Pro Arg Glu Pro Phe Gly Arg Lys His Leu Lys Ala Ile
    370                 375                 380

Asp Val Asn Met Asn Lys Met Pro Asp Val Ala Met Thr Leu Ala Val
385                 390                 395                 400

Val Ala Leu Phe Ala Asp Gly Pro Thr Ala Ile Arg Asp Val Ala Ser
                405                 410                 415

Trp Arg Val Lys Glu Thr Glu Arg Met Val Ala Ile Arg Thr Glu Leu
            420                 425                 430

Thr Lys Leu Gly Ala Ser Val Glu Glu Gly Pro Asp Tyr Cys Ile Ile
        435                 440                 445

Thr Pro Pro Glu Lys Leu Asn Val Thr Ala Ile Asp Thr Tyr Asp Asp
    450                 455                 460

His Arg Met Ala Met Ala Phe Ser Leu Ala Ala Cys Ala Glu Val Pro
465                 470                 475                 480

Val Thr Ile Arg Asp Pro Gly Cys Thr Arg Lys Thr Phe Pro Asp Tyr
                485                 490                 495

Phe Asp Val Leu Ser Thr Phe Val Lys Asn
            500                 505
```

<210> SEQ ID NO 4
<211> LENGTH: 1112
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

```
atgttactat ggtgccttct tatcccactg agcattggta tatttagagg tttttgttga     60

acatgcctaa atcatctcaa tcaacgatgg acaatctttt cttcgattga gctgaggtac    120
```

-continued

```
gtcatctaca ggataggacc ttgagaatat gtgtccgtca atagctaacc ctctactaat    180

tttttcaatc aagcaaccta ttggcttgac tttaattcgt accggcttct actacttcta    240

cagtattttg tctctataaa ttgcagctac aacagtcaga acggctggct ttaaaatcaa    300

atggcctaag gatcattgaa aggcatctta gcaatgtcta aaattattac cttctctaga    360

cgttgatgtc ttatagggct tggacatgac acagacataa tttatatagt attagattga    420

gtgagactgg gtgggtttaa attccaagca agtcaaactt gttcttaatt ttttccaatc    480

ccattcaatc catgggtaac gggattaacc gaacaatgtc ttatagggct tggacatgac    540

acagacataa tttatatagt attagtgccg gtaccacacg ggtctaatgt cgtgtttagg    600

cctccatccg gcatgatgat tggcataagc acgacatgat taggtggtcg acacgattaa    660

gcacggctta aaccagctag tagtatgtag atgtgattgt gatatgtata tgtgattgtg    720

aattgtgatt tattatggtt ttaagtataa tcaatttact ttataatggt ataaatgttt    780

aaattctaaa actgtatata taattttaaa gattttctat aattctagac tgacacaaat    840

actattagtt gttaatgtta tatagtgccg gtatgataca attaaatatt atagtgtagt    900

gtctagatct acactagtgc cgacacgaca caatataatt agtaatagtg cttaataata    960

cttagtgtac ctactgggcg gttcgtctgg ctatctataa tcatgaatac tcgtgtgctc   1020

gtcaccggtc acggccagga gatatgacga cggctgttgt tttcttctgg cgtggggctg   1080

cgcgaaggga taagaaggca ccatagtaac at                                 1112


<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

atgttactat ggtgccttct tatcc                                           25


<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

ggataagaag gcaccatagt aacat                                           25


<210> SEQ ID NO 7
<211> LENGTH: 367
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

atgttactat ggtgccttct tatcccactg agcattggta tatttagagg tttttgttga     60

acatgcctaa atcatctcaa tcaacgatgg acaatctttt cttcgattga gctgaggtac    120

gtcatctaca ggataggacc ttgagaatat gtgtccgtca atagctaacc ctctactaat    180

tttttcaatc aagcaaccta ttggcttgac tttaattcgt accggcttct actacttcta    240
```

```
cagtattttg tctctataaa ttgcagctac aacagtcaga acggctggct ttaaaatcaa    300

atggcctaag gatcattgaa aggcatctta gcaatgtcta aaattattac cttctctaga    360

cgttgat                                                              367
```

<210> SEQ ID NO 8
<211> LENGTH: 745
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 8

```
gtcttatagg gcttggacat gacacagaca taatttatat agtattagat tgagtgagac     60

tgggtgggtt taaattccaa gcaagtcaaa cttgttctta attttttcca atcccattca    120

atccatgggt aacgggatta accgaacaat gtcttatagg gcttggacat gacacagaca    180

taatttatat agtattagtg ccggtaccac acgggtctaa tgtcgtgttt aggcctccat    240

ccggcatgat gattggcata agcacgacat gattaggtgg tcgacacgat taagcacggc    300

ttaaaccagc tagtagtatg tagatgtgat tgtgatatgt atatgtgatt gtgaattgtg    360

atttattatg gttttaagta taatcaattt actttataat ggtataaatg tttaaattct    420

aaaactgtat atataatttt aaagattttc tataattcta gactgacaca aatactatta    480

gttgttaatg ttatatagtg ccggtatgat acaattaaat attatagtgt agtgtctaga    540

tctacactag tgccgacacg acacaatata attagtaata gtgcttaata atacttagtg    600

tacctactgg gcggttcgtc tggctatcta taatcatgaa tactcgtgtg ctcgtcaccg    660

gtcacggcca ggagatatga cgacggctgt tgttttcttc tggcgtgggg ctgcgcgaag    720

ggataagaag gcaccatagt aacat                                          745
```

<210> SEQ ID NO 9
<211> LENGTH: 725
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9

```
gtcttatagg gcttggacat gacacagaca taatttatat agtattagat tgagtgagac     60

tgggtgggtt taaattccaa gcaagtcaaa cttgttctta attttttcca atcccattca    120

atccatgggt aacgggatta accgaacaat gtcttatagg gcttggacat gacacagaca    180

taatttatat agtattagtg ccggtaccac acgggtctaa tgtcgtgttt aggcctccat    240

ccggcatgat gattggcata agcacgacat gattaggtgg tcgacacgat taagcacggc    300

ttaaaccagc tagtagtatg tagatgtgat tgtgatatgt atatgtgatt gtgaattgtg    360

atttattatg gttttaagta taatcaattt actttataat ggtataaatg tttaaattct    420

aaaactgtat atataatttt aaagattttc tataattcta gactgacaca aatactatta    480

gttgttaatg ttatatagtg ccggtatgat acaattaaat attatagtgt agtgtctaga    540

tctacactag tgccgacacg acacaatata attagtaata gtgcttaata atacttagtg    600

tacctactgg gcggttcgtc tggctatcta taatcatgaa tactcgtgtg ctcgtcaccg    660

gtcacggcca ggagatatga cgacggctgt tgttttcttc tggcgtgggg ctgcgcgaag    720

ggata                                                                725
```

-continued

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
cgcccagtag gtacactaag 20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
cttagtgtac ctactgggcg 20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 12
agacgttgat gtcttatagg 20

<210> SEQ ID NO 13
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 13
taccttctct agacgttgat gtcttatagg gcttggacat 40

<210> SEQ ID NO 14
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 14
ctaaaattat taccttctct agacgttgat gtcttatagg gcttggacat gacacagaca 60

<210> SEQ ID NO 15
<211> LENGTH: 1092
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15
atgttactat ggtgccttct tatcccactg agcattggta tatttagagg tttttgttga 60

-continued

```
acatgcctaa atcatctcaa tcaacgatgg acaatctttt cttcgattga gctgaggtac    120

gtcatctaca ggataggacc ttgagaatat gtgtccgtca atagctaacc ctctactaat    180

tttttcaatc aagcaaccta ttggcttgac tttaattcgt accggcttct actacttcta    240

cagtattttg tctctataaa ttgcagctac aacagtcaga acggctggct ttaaaatcaa    300

atggcctaag gatcattgaa aggcatctta gcaatgtcta aaattattac cttctctaga    360

cgttgatgtc ttatagggct tggacatgac acagacataa tttatatagt attagattga    420

gtgagactgg gtgggtttaa attccaagca agtcaaactt gttcttaatt ttttccaatc    480

ccattcaatc catgggtaac gggattaacc gaacaatgtc ttatagggct tggacatgac    540

acagacataa tttatatagt attagtgccg gtaccacacg ggtctaatgt cgtgtttagg    600

cctccatccg gcatgatgat tggcataagc acgacatgat taggtggtcg acacgattaa    660

gcacggctta aaccagctag tagtatgtag atgtgattgt gatatgtata tgtgattgtg    720

aattgtgatt tattatggtt ttaagtataa tcaatttact ttataatggt ataaatgttt    780

aaattctaaa actgtatata taattttaaa gatttctat aattctagac tgacacaaat    840

actattagtt gttaatgtta tatagtgccg gtatgataca attaaatatt atagtgtagt    900

gtctagatct acactagtgc cgacacgaca caatataatt agtaatagtg cttaataata    960

cttagtgtac ctactgggcg gttcgtctgg ctatctataa tcatgaatac tcgtgtgctc   1020

gtcaccggtc acggccagga gatatgacga cggctgttgt tttcttctgg cgtggggctg   1080

cgcgaaggga ta                                                        1092
```

<210> SEQ ID NO 16
<211> LENGTH: 6755
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

```
atcgattgca accttcaaat tctcttcgat cttccttcca aattcatcta atatttcatc     60

ctcggcaagg aaatcttcta acgtgtaaac ttcactggga tccaactcga aaggatcaaa    120

ctctccctct ggttcgtttg acattgtgga tggagtgact aacctgctaa caccctgcaa    180

caatttatac aggagcatat cctcatgcac acgcaaaact gatgttgtcc acaagacacg    240

cacaggacac gcacaggaca cgcaaacagt ttcagactca tgcacacgca catcagtttc    300

agactcaggc acacgcacat caaatcacct tcgcttgtcg atgagtcgca gccgcatcgt    360

acaatggcga ttttaccgac gataaggcat gggagcacga gccgtcgccg tcgccttgcg    420

agacgacggg agcgatctct cccttcattt aatctcttcc acgtcaggtt attttgctga    480

gatggcagta tacagacggc aaagttaatg ccgttgtaca tgcccttaga ctcttccgtc    540

accaactcac ttagattttt acaacggaac ataaggttcg cttgcagact tacatataag    600

gtatagttgc ataataatcg ccttatgctg tacattgcga cacccgtaaa tattcgatga    660

aatattagta cacaatatta aataagaacg aacaatacat atattatcat tgatcttagt    720

atctcctttt gctcctcgta gaacaattct gtgtaaatta tgcgtaaaat tcgaggacca    780

aaacattggc tagaaaaata cctaaaatca gttttgcaat tgtttctgat tttcctcata    840

ttttcttgct tataaagttt tccaaaagta ccattttgga tgaaaaaacg gaaaacaacg    900

ctggtctact tgtaaatttg gtagtgacat ttgggaccgt ctagacacga cctaaaaata    960
```

-continued

```
gtagtctaaa acatagtctg acacgatgcc ttaaaaatag acgacaaagc acaacacgat   1020
tagatgtgtc gtgttttgac cgacacgaca caaagtaagg cacgatttaa aacccaataa   1080
ataatatttt aatggttatt ttatgttcca ataattttca tctcttcaaa aaaatgttat   1140
agaaatcatt gatacttagt tgaatatcct aacacaatat atatatatat attaatatat   1200
atatatatca attttaagtc actttgctag acatagtaat atattttaaa tattttctct   1260
ttcttgtata tttttaaaat acacatcagt ttttatatgt gtcgtgcttg aaccgacacg   1320
atataatcat cggttcgccg tacttctaga tcatgatgtt cctaggtttt aatattaaga   1380
gacggtctat attaactcaa aactatttcg tgaaaggcta actcgaaaaa aaaatgaatg   1440
taatcacggc ccgtcctgga ttcgagattc taacgtttca ttcgtgtcca gtgtgcacac   1500
ttgtggaaaa ggaagacgaa gaaaaaaacc aacaactaac tccggcccgc cggatgcgcc   1560
cacctacttc cccctcgccc ctctcatggt ctctctcgcg cccagatctg ctactagacg   1620
gcaccgctgc agcgcgtcgt gtcgcggggg ttggtggcag gcagcgagag cttgccgttc   1680
ctctctctca gttgtcaggt cctaggctca cctcaccggc tcccagcccg cttctatttc   1740
ttcctccccg accccgtgca ggtggcagtc cagtccacgc caccaaccgc gaggcgaacc   1800
aaaccaaccc actctcccca accccgcgcg cccaggccgc ccgccctacc aaccatcggc   1860
gtcggcaatg gcggccatgg cgaccaaggc cgccgcgggc accgtgtcgc tggacctcgc   1920
cgcgccgtcg cgccgccacc accgcccgag ctcggcgcgc ccgcccgccc gccccgccgt   1980
ccgcgggctg cgggcgcctg ggcgccgcgt gatcgccgcg ccgccggcgg cggcagcggc   2040
ggcggcggtg caggcgggtg ccgaggagat cgtgctgcag cccatcaagg agatctccgg   2100
caccgtcaag ctgccggggt ccaagtcgct ttccaaccgg atcctcctgc tcgccgccct   2160
gtccgaggtg agcgattttg gtgcttgctg cgctgccctg tctcactgct acctaaatgt   2220
tttgcctgtc gaataccatg gattctcggt gtaatccatc tcacgatcag atgcaccgca   2280
tgtcgcatgc ctagctctct ctaatttgtc tagtagtttg tatacggatt aatattgata   2340
aatcggtacc gcaaaagcta ggtgtaaata aacactagaa aattggatgt tcccctatcg   2400
gcctgtactc ggctactcgt tcttgtgatg gcatgctgtc tcttcttggt gtttggtgaa   2460
caaccttatg aaatttgggc gcaaagaact cgccctcaag ggttgatctt atgccatcgt   2520
catgataaac agtggagcac ggacgatcct ttacgttgtt tttaacaaac tttgtcagaa   2580
aactagcatc attaacttct taatgacgat ttcacaacaa aaaaaggtaa cctcgctact   2640
aacataacaa aatacttgtt gcttattaat tatatgtttt ttaatctttg atcaggggac   2700
aacagtggtt gataacctgt tgaacagtga ggatgtccac tacatgctcg gggccttgag   2760
gactcttggt ctctctgtcg aagcggacaa agctgccaaa agagctgtag ttgttggctg   2820
tggtggaaag ttcccagttg aggattctaa agaggaagtg cagctcttct tggggaatgc   2880
tggaattgca atgcggtcat tgacagcagc tgttactgct gctggtggaa atgcaacgta   2940
tgtttcctct ctttctctct acaatacttg ctggagttag tatgaaaccc atgggtatgt   3000
ctagtggctt atggtgtatt ggtttttgaa cttcagttac gtgcttgatg gagtaccaag   3060
aatgagggag agacccattg gcgacttggt tgtcggattg aagcagcttg gtgcagatgt   3120
tgattgtttc cttggcactg actgcccacc tgttcgtgtc aatggaatcg gagggctacc   3180
tggtggcaag gttagctact aagggccaca tgttacattc ttctgtaaat ggtacaacta   3240
ttgtcgagct tttgcatttg taaggaaagc attgattgat ctgaatttga tgctacacca   3300
caaaatatcc tacaaatggt catccctaac tagcaaacaa tgaagtaata cttggcatgt   3360
```

-continued

```
gtttatcaaa ttaatttcca tcttctgggg cattgcctgt tttctagtct aatagcattt   3420
gtttttagca ttaattagct cttacaattg ttatgttcta caggtcaagc tgtctggctc   3480
catcagcagt cagtacttga gtgccttgct gatggctgct cctttggctc ttggggatgt   3540
ggagattgaa atcattgata aattaatctc cattccctac gtcgaaatga cattgagatt   3600
gatggagcgt tttggtgtga aagcagagca ttctgatagc tgggacagat tctacattaa   3660
gggaggtcaa aaatacaagt aagctctgta atgtatttca ctactttgat gccaatgttt   3720
cagttttcag ttttccaaac agtcgcatca atatttgaat agatgcactg tagaaaaaaa   3780
atcattgcag ggaaaaacta gtactgagta ttttgactgt aaattatttt accagtcgga   3840
atatagtcag tctattggag tcaagagcgt gaaccgaaat agccagttaa ttatcccatt   3900
atacagagga caaccatgta tactattgaa acttggttta taagagaatc taggtagctg   3960
gactcgtagc tgcttggcat ggataccttc ttatctttag gaaaagacac ttgatttttt   4020
ttttctgtgg ccctctatga tgtgtgaacc tgcttctcta ttgctttaga aggatatatc   4080
tatgtcgtta tgcaacatgc ttcccttagc catttgtact gaaatcagtt tcataagttc   4140
gttagtggtt ccctaaacga aaccttgttt ttctttgcaa tcaacaggtc ccctaaaaat   4200
gcctatgttg aaggtgatgc ctcaagcgca agctatttct tggctggtgc tgcaattact   4260
ggagggactg tgactgtgga aggttgtggc accaccagtt tgcaggtaaa gatttcttgg   4320
ctggtgctac aataactgct tttgtctttt tggtttcagc attgttctca gagtcactaa   4380
ataacattat catctgcaaa tgtcaaatag acatacttag gtgaattcat gtaaccgttt   4440
ccttacaaat ttgctgaaac ctcagggtga tgtgaagttt gctgaggtac tggagatgat   4500
gggagcgaag gttacatgga ccgagactag cgtaactgtt actggcccac cgcgggagcc   4560
atttgggagg aaacacctca aggcgattga tgtcaacatg aacaagatgc ctgatgtcgc   4620
catgactctt gctgtggttg ccctctttgc cgatggcccg acagccatca gagacggtaa   4680
aacattctca gccctacaac catgcctctt ctacatcact acttgacaag actaaaaact   4740
attggctcgt tggcagtggc ttcctggaga gtaaaggaga ccgagaggat ggttgcgatc   4800
cggacggagc taaccaaggt aaggctacat acttcacatg tctcacgtcg tctttccata   4860
gctcgctgcc tcttagcggc ttgcctgcgg tcgctccatc ctcggttgct gtctgtgttt   4920
tccacagctg ggagcatctg ttgaggaagg gccggactac tgcatcatca cgccgccgga   4980
gaagctgaac gtgacggcga tcgacacgta cgacgaccac aggatggcca tggccttctc   5040
ccttgccgcc tgtgccgagg tccccgtgac catccgggac cctgggtgca cccggaagac   5100
cttccccgac tacttcgatg tgctgagcac tttcgtcaag aattaataaa gcgtgcgata   5160
ctaccacgca gcttgattga agtgataggc ttgtgctgag gaaatacatt tcttttgttc   5220
tgtttttttct ctttcacggg attaagtttt gagtctgtaa cgttagttgt ttgtagcaag   5280
tttctatttc ggatcttaag tttgtgcact gtaagccaaa tttcatttca agagtggttc   5340
gttggaataa taagaataat aaattacgtt tcagtggctg tcaagcctgc tgctacgttt   5400
taggagatgg cattagacat tcatcatcaa caacaataaa accttttagc ctcaaacaat   5460
aatagtgaag ttattttttta gtcctaaaca agttgcatta ggatatagtt aaaacacaaa   5520
agaagctaaa gttagggttt agacatgtgg atattgtttt ccatgtatag tatgttcttt   5580
ctttgagtct catttaacta cctctacaca taccaacttt agtttttttt ctacctcttc   5640
atgttactat ggtgccttct tatcccactg agcattggta tatttagagg tttttgttga   5700
```

-continued

```
acatgcctaa atcatctcaa tcaacgatgg acaatctttt cttcgattga gctgaggtac   5760

gtcatctaca ggataggacc ttgagaatat gtgtccgtca atagctaacc ctctactaat   5820

tttttcaatc aagcaaccta ttggcttgac tttaattcgt accggcttct actacttcta   5880

cagtattttg tctctataaa ttgcagctac aacagtcaga acggctggct ttaaaatcaa   5940

atggcctaag gatcattgaa aggcatctta gcaatgtcta aaattattac cttctctaga   6000

cgttgatatc gtcttatagg gcttggacat gacacagaca taatttatat agtattagat   6060

tgagtgagac tgggtgggtt taaattccaa gcaagtcaaa cttgttctta attttttcca   6120

atcccattca atccatgggt aacgggatta accgaacaat gtcttatagg gcttggacat   6180

gacacagaca taatttatat agtattagtg ccggtaccac acgggtctaa tgtcgtgttt   6240

aggcctccat ccggcatgat gattggcata agcacgacat gattaggtgg tcgacacgat   6300

taagcacggc ttaaaccagc tagtagtatg tagatgtgat tgtgatatgt atatgtgatt   6360

gtgaattgtg atttattatg gttttaagta taatcaattt actttataat ggtataaatg   6420

tttaaattct aaaactgtat atataatttt aaagattttc tataattcta gactgacaca   6480

aatactatta gttgttaatg ttatatagtg ccggtatgat acaattaaat attatagtgt   6540

agtgtctaga tctacactag tgccgacacg acacaatata attagtaata gtgcttaata   6600

atacttagtg tacctactgg gcggttcgtc tggctatcta taatcatgaa tactcgtgtg   6660

ctcgtcaccg gtcacggcca ggagatatga cgacggctgt tgttttcttc tggcgtgggg   6720

ctgcgcgaag ggataagaag gcaccatagt aacat                              6755
```

<210> SEQ ID NO 17
<211> LENGTH: 6735
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
atcgattgca accttcaaat tctcttcgat cttccttcca aattcatcta atatttcatc     60

ctcggcaagg aaatcttcta acgtgtaaac ttcactggga tccaactcga aaggatcaaa    120

ctctccctct ggttcgtttg acattgtgga tggagtgact aacctgctaa caccctgcaa    180

caatttatac aggagcatat cctcatgcac acgcaaaact gatgttgtcc acaagacacg    240

cacaggacac gcacaggaca cgcaaacagt ttcagactca tgcacacgca catcagtttc    300

agactcaggc acacgcacat caaatcacct tcgcttgtcg atgagtcgca gccgcatcgt    360

acaatggcga ttttaccgac gataaggcat gggagcacga gccgtcgccg tcgccttgcg    420

agacgacggg agcgatctct cccttcattt aatctcttcc acgtcaggtt attttgctga    480

gatggcagta tacagacggc aaagttaatg ccgttgtaca tgcccttaga ctcttccgtc    540

accaactcac ttagattttt acaacggaac ataaggttcg cttgcagact tacatataag    600

gtatagttgc ataataatcg ccttatgctg tacattgcga cacccgtaaa tattcgatga    660

aatattagta cacaatatta aataagaacg aacaatacat atattatcat tgatcttagt    720

atctcctttt gctcctcgta gaacaattct gtgtaaatta tgcgtaaaat tcgaggacca    780

aaacattggc tagaaaaata cctaaaatca gttttgcaat tgtttctgat tttcctcata    840

ttttcttgct tataaagttt tccaaaagta ccattttgga tgaaaaaacg gaaaacaacg    900

ctggtctact tgtaaatttg gtagtgacat ttgggaccgt ctagacacga cctaaaaata    960
```

```
gtagtctaaa acatagtctg acacgatgcc ttaaaaatag acgacaaagc acaacacgat   1020
tagatgtgtc gtgttttgac cgacacgaca caaagtaagg cacgatttaa aacccaataa   1080
ataatatttt aatggttatt ttatgttcca ataattttca tctcttcaaa aaaatgttat   1140
agaaatcatt gatacttagt tgaatatcct aacacaatat atatatatat attaatatat   1200
atatatatca attttaagtc actttgctag acatagtaat atattttaaa tattttctct   1260
ttcttgtata tttttaaaat acacatcagt ttttatatgt gtcgtgcttg aaccgacacg   1320
atataatcat cggttcgccg tacttctaga tcatgatgtt cctaggtttt aatattaaga   1380
gacggtctat attaactcaa aactatttcg tgaaaggcta actcgaaaaa aaaatgaatg   1440
taatcacggc ccgtcctgga ttcgagattc taacgtttca ttcgtgtcca gtgtgcacac   1500
ttgtggaaaa ggaagacgaa gaaaaaaacc aacaactaac tccggcccgc cggatgcgcc   1560
cacctacttc cccctcgccc ctctcatggt ctctctcgcg cccagatctg ctactagacg   1620
gcaccgctgc agcgcgtcgt gtcgcggggg ttggtggcag gcagcgagag cttgccgttc   1680
ctctctctca gttgtcaggt cctaggctca cctcaccggc tcccagcccg cttctatttc   1740
ttcctccccg accccgtgca ggtggcagtc cagtccacgc caccaaccgc gaggcgaacc   1800
aaaccaaccc actctcccca accccgcgcg cccaggccgc ccgccctacc aaccatcggc   1860
gtcggcaatg gcggccatgg cgaccaaggc cgccgcgggc accgtgtcgc tggacctcgc   1920
cgcgccgtcg cgccgccacc accgcccgag ctcggcgcgc ccgcccgccc gccccgccgt   1980
ccgcgggctg cgggcgcctg ggcgccgcgt gatcgccgcg ccgccggcgg cggcagcggc   2040
ggcggcggtg caggcgggtg ccgaggagat cgtgctgcag cccatcaagg agatctccgg   2100
caccgtcaag ctgccggggt ccaagtcgct ttccaaccgg atcctcctgc tcgccgccct   2160
gtccgaggtg agcgattttg gtgcttgctg cgctgccctg tctcactgct acctaaatgt   2220
tttgcctgtc gaataccatg gattctcggt gtaatccatc tcacgatcag atgcaccgca   2280
tgtcgcatgc ctagctctct ctaatttgtc tagtagtttg tatacggatt aatattgata   2340
aatcggtacc gcaaaagcta ggtgtaaata aacactagaa aattggatgt tcccctatcg   2400
gcctgtactc ggctactcgt tcttgtgatg gcatgctgtc tcttcttggt gtttggtgaa   2460
caaccttatg aaatttgggc gcaaagaact cgccctcaag ggttgatctt atgccatcgt   2520
catgataaac agtggagcac ggacgatcct ttacgttgtt tttaacaaac tttgtcagaa   2580
aactagcatc attaacttct taatgacgat ttcacaacaa aaaaaggtaa cctcgctact   2640
aacataacaa aatacttgtt gcttattaat tatatgtttt ttaatctttg atcaggggac   2700
aacagtggtt gataacctgt tgaacagtga ggatgtccac tacatgctcg gggccttgag   2760
gactcttggt ctctctgtcg aagcggacaa agctgccaaa agagctgtag ttgttggctg   2820
tggtggaaag ttcccagttg aggattctaa agaggaagtg cagctcttct tggggaatgc   2880
tggaattgca atgcggtcat tgacagcagc tgttactgct gctggtggaa atgcaacgta   2940
tgtttcctct ctttctctct acaatacttg ctggagttag tatgaaaccc atgggtatgt   3000
ctagtggctt atggtgtatt ggtttttgaa cttcagttac gtgcttgatg gagtaccaag   3060
aatgagggag agacccattg gcgacttggt tgtcggattg aagcagcttg gtgcagatgt   3120
tgattgtttc cttggcactg actgcccacc tgttcgtgtc aatggaatcg gagggctacc   3180
tggtggcaag gttagctact aagggccaca tgttacattc ttctgtaaat ggtacaacta   3240
ttgtcgagct tttgcatttg taaggaaagc attgattgat ctgaatttga tgctacacca   3300
caaaatatcc tacaaatggt catccctaac tagcaaacaa tgaagtaata cttggcatgt   3360
```

gtttatcaaa ttaatttcca tcttctgggg cattgcctgt tttctagtct aatagcattt 3420
gtttttagca ttaattagct cttacaattg ttatgttcta caggtcaagc tgtctggctc 3480
catcagcagt cagtacttga gtgccttgct gatggctgct cctttggctc ttggggatgt 3540
ggagattgaa atcattgata aattaatctc cattccctac gtcgaaatga cattgagatt 3600
gatggagcgt tttggtgtga aagcagagca ttctgatagc tgggacagat tctacattaa 3660
gggaggtcaa aaatacaagt aagctctgta atgtatttca ctactttgat gccaatgttt 3720
cagttttcag ttttccaaac agtcgcatca atatttgaat agatgcactg tagaaaaaaa 3780
atcattgcag ggaaaaacta gtactgagta ttttgactgt aaattatttt accagtcgga 3840
atatagtcag tctattggag tcaagagcgt gaaccgaaat agccagttaa ttatcccatt 3900
atacagagga caaccatgta tactattgaa acttggttta taagagaatc taggtagctg 3960
gactcgtagc tgcttggcat ggataccttc ttatctttag gaaaagacac ttgatttttt 4020
ttttctgtgg ccctctatga tgtgtgaacc tgcttctcta ttgctttaga aggatatatc 4080
tatgtcgtta tgcaacatgc ttcccttagc catttgtact gaaatcagtt tcataagttc 4140
gttagtggtt ccctaaacga aaccttgttt ttctttgcaa tcaacaggtc ccctaaaaat 4200
gcctatgttg aaggtgatgc ctcaagcgca agctatttct tggctggtgc tgcaattact 4260
ggagggactg tgactgtgga aggttgtggc accaccagtt tgcaggtaaa gatttcttgg 4320
ctggtgctac aataactgct tttgtctttt tggtttcagc attgttctca gagtcactaa 4380
ataacattat catctgcaaa tgtcaaatag acatacttag gtgaattcat gtaaccgttt 4440
ccttacaaat ttgctgaaac ctcagggtga tgtgaagttt gctgaggtac tggagatgat 4500
gggagcgaag gttacatgga ccgagactag cgtaactgtt actggcccac cgcgggagcc 4560
atttgggagg aaacacctca aggcgattga tgtcaacatg aacaagatgc ctgatgtcgc 4620
catgactctt gctgtggttg ccctctttgc cgatggcccg acagccatca gagacggtaa 4680
aacattctca gccctacaac catgcctctt ctacatcact acttgacaag actaaaaact 4740
attggctcgt tggcagtggc ttcctggaga gtaaaggaga ccgagaggat ggttgcgatc 4800
cggacggagc taaccaaggt aaggctacat acttcacatg tctcacgtcg tctttccata 4860
gctcgctgcc tcttagcggc ttgcctgcgg tcgctccatc ctcggttgct gtctgtgttt 4920
tccacagctg ggagcatctg ttgaggaagg gccggactac tgcatcatca cgccgccgga 4980
gaagctgaac gtgacggcga tcgacacgta cgacgaccac aggatggcca tggccttctc 5040
ccttgccgcc tgtgccgagg tccccgtgac catccgggac cctgggtgca cccggaagac 5100
cttccccgac tacttcgatg tgctgagcac tttcgtcaag aattaataaa gcgtgcgata 5160
ctaccacgca gcttgattga agtgataggc ttgtgctgag gaaatacatt tcttttgttc 5220 tgtttttttct ctttcacggg attaagtttt gagtctgtaa cgttagttgt ttgtagcaag 5280
tttctatttc ggatcttaag tttgtgcact gtaagccaaa tttcatttca agagtggttc 5340
gttggaataa taagaataat aaattacgtt tcagtggctg tcaagcctgc tgctacgttt 5400
taggagatgg cattagacat tcatcatcaa caacaataaa accttttagc ctcaaacaat 5460
aatagtgaag ttatttttta gtcctaaaca agttgcatta ggatatagtt aaaacacaaa 5520
agaagctaaa gttagggttt agacatgtgg atattgtttt ccatgtatag tatgttcttt 5580
ctttgagtct catttaacta cctctacaca taccaacttt agtttttttt ctacctcttc 5640
atgttactat ggtgccttct tatcccactg agcattggta tatttagagg tttttgttga 5700

-continued acatgcctaa atcatctcaa tcaacgatgg acaatctttt cttcgattga gctgaggtac 5760
gtcatctaca ggataggacc ttgagaatat gtgtccgtca atagctaacc ctctactaat 5820
tttttcaatc aagcaaccta ttggcttgac tttaattcgt accggcttct actacttcta 5880
cagtattttg tctctataaa ttgcagctac aacagtcaga acggctggct ttaaaatcaa 5940
atggcctaag gatcattgaa aggcatctta gcaatgtcta aaattattac cttctctaga 6000
cgttgatatc gtcttatagg gcttggacat gacacagaca taatttatat agtattagat 6060
tgagtgagac tgggtgggtt taaattccaa gcaagtcaaa cttgttctta attttttcca 6120
atcccattca atccatgggt aacgggatta accgaacaat gtcttatagg gcttggacat 6180
gacacagaca taatttatat agtattagtg ccggtaccac acgggtctaa tgtcgtgttt 6240
aggcctccat ccggcatgat gattggcata agcacgacat gattaggtgg tcgacacgat 6300
taagcacggc ttaaaccagc tagtagtatg tagatgtgat tgtgatatgt atatgtgatt 6360
gtgaattgtg atttattatg gttttaagta taatcaattt actttataat ggtataaatg 6420
tttaaattct aaaactgtat atataatttt aaagattttc tataattcta gactgacaca 6480
aatactatta gttgttaatg ttatatagtg ccggtatgat acaattaaat attatagtgt 6540
agtgtctaga tctacactag tgccgacacg acacaatata attagtaata gtgcttaata 6600
atacttagtg tacctactgg gcggttcgtc tggctatcta taatcatgaa tactcgtgtg 6660
ctcgtcaccg gtcacggcca ggagatatga cgacggctgt tgttttcttc tggcgtgggg 6720
ctgcgcgaag ggata 6735

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 18
cattgaaagg catcttagca atgtctaaa 29

<210> SEQ ID NO 19
<211> LENGTH: 31
<212> TYPE: DNA
<213> ORGANISM: Artificial Sequence
<220> FEATURE:
<223> OTHER INFORMATION: Description of Artificial Sequence: Synthetic
primer

<400> SEQUENCE: 19
ccacccagtc tcactcaatc taatactata t 31

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
probe

<400> SEQUENCE: 20
ccaagcccta taagacatca a 21

<210> SEQ ID NO 21
<211> LENGTH: 2346
<212> TYPE: DNA

-continued

<213> ORGANISM: Artificial Sequence
<220> FEATURE:
<223> OTHER INFORMATION: Description of Artificial Sequence: Synthetic
A/C probe

<400> SEQUENCE: 21
atcgattgca accttcaaat tctcttcgat cttccttcca aattcatcta atatttcatc 60
ctcggcaagg aaatcttcta acgtgtaaac ttcactggga tccaactcga aaggatcaaa 120
ctctccctct ggttcgtttg acattgtgga tggagtgact aacctgctaa caccctgcaa 180
caatttatac aggagcatat cctcatgcac acgcaaaact gatgttgtcc acaagacacg 240
cacaggacac gcacaggaca cgcaaacagt ttcagactca tgcacacgca catcagtttc 300
agactcaggc acacgcacat caaatcacct tcgcttgtcg atgagtcgca gccgcatcgt 360
acaatggcga ttttaccgac gataaggcat gggagcacga gccgtcgccg tcgccttgcg 420
agacgacggg agcgatctct cccttcattt aatctcttcc acgtcaggtt attttgctga 480
gatggcagta tacagacggc aaagttaatg ccgttgtaca tgcccttaga ctcttccgtc 540
accaactcac ttagattttt acaacggaac ataaggttcg cttgcagact tacatataag 600
gtatagttgc ataataatcg ccttatgctg tacattgcga cacccgtaaa tattcgatga 660
aatattagta cacaatatta aataagaacg aacaatacat atattatcat tgatcttagt 720
atctcctttt gctcctcgta gaacaattct gtgtaaatta tgcgtaaaat tcgaggacca 780
aaacattggc tagaaaaata cctaaaatca gttttgcaat tgtttctgat tttcctcata 840
ttttcttgct tataaagttt tccaaaagta ccattttgga tgaaaaaacg gaaaacaacg 900
ctggtctact tgtaaatttg gtagtgacat ttgggaccgt ctagacacga cctaaaaata 960
gtagtctaaa acatagtctg acacgatgcc ttaaaaatag acgacaaagc acaacacgat 1020
tagatgtgtc gtgttttgac cgacacgaca caaagtaagg cacgatttaa aacccaataa 1080
ataatatttt aatggttatt ttatgttcca ataattttca tctcttcaaa aaaatgttat 1140
agaaatcatt gatacttagt tgaatatcct aacacaatat atatatatat attaatatat 1200
atatatatca attttaagtc actttgctag acatagtaat atattttaaa tattttctct 1260
ttcttgtata tttttaaaat acacatcagt ttttatatgt gtcgtgcttg aaccgacacg 1320
atataatcat cggttcgccg tacttctaga tcatgatgtt cctaggtttt aatattaaga 1380
gacggtctat attaactcaa aactatttcg tgaaaggcta actcgaaaaa aaaatgaatg 1440
taatcacggc ccgtcctgga ttcgagattc taacgtttca ttcgtgtcca gtgtgcacac 1500
ttgtggaaaa ggaagacgaa gaaaaaaacc aacaactaac tccggcccgc cggatgcgcc 1560
cacctacttc cccctcgccc ctctcatggt ctctctcgcg cccagatctg ctactagacg 1620
gcaccgctgc agcgcgtcgt gtcgcggggg ttggtggcag gcagcgagag cttgccgttc 1680
ctctctctca gttgtcaggt cctaggctca cctcaccggc tcccagcccg cttctatttc 1740
ttcctccccg accccgtgca ggtggcagtc cagtccacgc caccaaccgc gaggcgaacc 1800
aaaccaaccc actctcccca accccgcgcg cccaggccgc ccgccctacc aaccatcggc 1860
gtcggcaatg gcggccatgg cgaccaaggc cgccgcgggc accgtgtcgc tggacctcgc 1920
cgcgccgtcg cgccgccacc accgcccgag ctcggcgcgc ccgcccgccc gccccgccgt 1980
ccgcgggctg cgggcgcctg ggcgccgcgt gatcgccgcg ccgccggcgg cggcagcggc 2040

```
ggcggcggtg caggcgggtg ccgaggagat cgtgctgcag cccatcaagg agatctccgg   2100

caccgtcaag ctgccggggt ccaagtcgct ttccaaccgg atcctcctgc tcgccgccct   2160

gtccgaggtg agcgattttg gtgcttgctg cgctgccctg tctcactgct acctaaatgt   2220

tttgcctgtc gaataccatg gattctcggt gtaatccatc tcacgatcag atgcaccgca   2280

tgtcgcatgc ctagctctct ctaatttgtc tagtagtttg tatacggatt aatattgata   2340

aatcgg                                                              2346
```

<210> SEQ ID NO 22
<211> LENGTH: 3664
<212> TYPE: DNA
<213> ORGANISM: Artificial Sequence
<220> FEATURE:
<223> OTHER INFORMATION: Description of Artificial Sequence: Synthetic A/E probe

<400> SEQUENCE: 22

```
taccgcaaaa gctaggtgta aataaacact agaaaattgg atgttcccct atcggcctgt     60

actcggctac tcgttcttgt gatggcatgc tgtctcttct tggtgtttgg tgaacaacct    120

tatgaaattt gggcgcaaag aactcgccct caagggttga tcttatgcca tcgtcatgat    180

aaacagtgga gcacggacga tcctttacgt tgtttttaac aaactttgtc agaaaactag    240

catcattaac ttcttaatga cgatttcaca acaaaaaaag gtaacctcgc tactaacata    300

acaaaatact tgttgcttat taattatatg ttttttaatc tttgatcagg ggacaacagt    360

ggttgataac ctgttgaaca gtgaggatgt ccactacatg ctcggggcct tgaggactct    420

tggtctctct gtcgaagcgg acaaagctgc caaaagagct gtagttgttg gctgtggtgg    480

aaagttccca gttgaggatt ctaaagagga agtgcagctc ttcttgggga atgctggaat    540

tgcaatgcgg tcattgacag cagctgttac tgctgctggt ggaaatgcaa cgtatgtttc    600

ctctctttct ctctacaata cttgctggag ttagtatgaa acccatgggt atgtctagtg    660

gcttatggtg tattggtttt tgaacttcag ttacgtgctt gatggagtac caagaatgag    720

ggagagaccc attggcgact tggttgtcgg attgaagcag cttggtgcag atgttgattg    780

tttccttggc actgactgcc cacctgttcg tgtcaatgga atcggagggc tacctggtgg    840

caaggttagc tactaagggc cacatgttac attcttctgt aaatggtaca actattgtcg    900

agcttttgca tttgtaagga aagcattgat tgatctgaat ttgatgctac accacaaaat    960

atcctacaaa tggtcatccc taactagcaa acaatgaagt aatacttggc atgtgtttat   1020

caaattaatt tccatcttct ggggcattgc ctgttttcta gtctaatagc atttgttttt   1080

agcattaatt agctcttaca attgttatgt tctacaggtc aagctgtctg gctccatcag   1140

cagtcagtac ttgagtgcct tgctgatggc tgctcctttg gctcttgggg atgtggagat   1200

tgaaatcatt gataaattaa tctccattcc ctacgtcgaa atgacattga gattgatgga   1260

gcgttttggt gtgaaagcag agcattctga tagctgggac agattctaca ttaagggagg   1320

tcaaaaatac aagtaagctc tgtaatgtat ttcactactt tgatgccaat gtttcagttt   1380

tcagttttcc aaacagtcgc atcaatattt gaatagatgc actgtagaaa aaaaatcatt   1440

gcagggaaaa actagtactg agtattttga ctgtaaatta ttttaccagt cggaatatag   1500

tcagtctatt ggagtcaaga gcgtgaaccg aaatagccag ttaattatcc cattatacag   1560

aggacaacca tgtatactat tgaaacttgg tttataagag aatctaggta gctggactcg   1620

tagctgcttg gcatggatac cttcttatct ttaggaaaag acacttgatt ttttttttct   1680
```

-continued

```
gtggccctct atgatgtgtg aacctgcttc tctattgctt tagaaggata tatctatgtc   1740
gttatgcaac atgcttccct tagccatttg tactgaaatc agtttcataa gttcgttagt   1800
ggttccctaa acgaaacctt gtttttcttt gcaatcaaca ggtcccctaa aaatgcctat   1860
gttgaaggtg atgcctcaag cgcaagctat ttcttggctg gtgctgcaat tactggaggg   1920
actgtgactg tggaaggttg tggcaccacc agtttgcagg taaagatttc ttggctggtg   1980
ctacaataac tgcttttgtc tttttggttt cagcattgtt ctcagagtca ctaaataaca   2040
ttatcatctg caaatgtcaa atagacatac ttaggtgaat tcatgtaacc gtttccttac   2100
aaatttgctg aaacctcagg gtgatgtgaa gtttgctgag gtactggaga tgatgggagc   2160
gaaggttaca tggaccgaga ctagcgtaac tgttactggc ccaccgcggg agccatttgg   2220
gaggaaacac ctcaaggcga ttgatgtcaa catgaacaag atgcctgatg tcgccatgac   2280
tcttgctgtg gttgccctct ttgccgatgg cccgacagcc atcagagacg gtaaaacatt   2340
ctcagcccta caaccatgcc tcttctacat cactacttga caagactaaa aactattggc   2400
tcgttggcag tggcttcctg gagagtaaag gagaccgaga ggatggttgc gatccggacg   2460
gagctaacca aggtaaggct acatacttca catgtctcac gtcgtctttc catagctcgc   2520
tgcctcttag cggcttgcct gcggtcgctc catcctcggt tgctgtctgt gttttccaca   2580
gctgggagca tctgttgagg aagggccgga ctactgcatc atcacgccgc cggagaagct   2640
gaacgtgacg gcgatcgaca cgtacgacga ccacaggatg gccatggcct tctcccttgc   2700
cgcctgtgcc gaggtccccg tgaccatccg ggaccctggg tgcacccgga agaccttccc   2760
cgactacttc gatgtgctga gcactttcgt caagaattaa taaagcgtgc gatactacca   2820
cgcagcttga ttgaagtgat aggcttgtgc tgaggaaata catttctttt gttctgtttt   2880
ttctctttca cgggattaag ttttgagtct gtaacgttag ttgtttgtag caagtttcta   2940
tttcggatct taagtttgtg cactgtaagc caaatttcat ttcaagagtg gttcgttgga   3000
ataataagaa taataaatta cgtttcagtg gctgtcaagc ctgctgctac gttttaggag   3060
atggcattag acattcatca tcaacaacaa taaaaccttt tagcctcaaa caataatagt   3120
gaagttattt tttagtccta aacaagttgc attaggatat agttaaaaca caaaagaagc   3180
taaagttagg gtttagacat gtggatattg ttttccatgt atagtatgtt ctttctttga   3240
gtctcattta actacctcta cacataccaa ctttagtttt ttttctacct cttcatgtta   3300
ctatggtgcc ttcttatccc actgagcatt ggtatattta gaggtttttg ttgaacatgc   3360
ctaaatcatc tcaatcaacg atggacaatc ttttcttcga ttgagctgag gtacgtcatc   3420
tacaggatag gaccttgaga atatgtgtcc gtcaatagct aaccctctac taattttttc   3480
aatcaagcaa cctattggct tgactttaat tcgtaccggc ttctactact tctacagtat   3540
tttgtctcta taaattgcag ctacaacagt cagaacggct ggctttaaaa tcaaatggcc   3600
taaggatcat tgaaaggcat cttagcaatg tctaaaatta ttaccttctc tagacgttga   3660
tatc                                                                3664
```

MAIZE EVENT HCEM485, COMPOSITIONS AND METHODS FOR DETECTING AND USE THEREOF

REFERENCE TO RELATED APPLICATION

This application is a divisional of previously filed and co-pending application U.S. Ser. No. 13/211,622, the contents of which are incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Aug. 3, 2011, is named 210010.txt and is 55,451 bytes in size.

BACKGROUND OF THE INVENTION

Glyphosate (N-phosphonomethylglycine) is a widely used active ingredient in herbicides. Glyphosate inhibits 5-enolpyruvyl-3-phosphoshikimic acid synthase (EPSP synthase, or EPSPS). EPSPS is involved in the synthesis of aromatic amino acids in plant cells. Inhibition of EPSPS effectively disrupts protein synthesis and thereby kills the affected plant cells. Because glyphosate is non-selective, it kills both weeds and crop plants. Thus it is useful with crop plants when one can modify the crop plants to be resistant to glyphosate, allowing the desirable plants to survive exposure to the glyphosate.

Recombinant DNA technology has been used to isolate mutant EPSP synthases that are glyphosate-resistant. Such glyphosate-resistant mutant EPSP synthase genes can be transformed into plants and confer glyphosate-resistance upon the transformed plants. By way of example, a glyphosate tolerant gene was isolated from *Agrobacterium* strain CP4 as described in U.S. Pat. No. 5,633,435. The full length maize EPSPS gene is described at U.S. Pat. No. 7,045,684. It is imported to the chloroplast and the chloroplast transit peptide cleaved, producing the mature EPSPS. See Herouet-Guicheney et al. (2009) “Safety evaluation of the double mutant 5-enolypyruvylshikimate-3-phosphate synthase (2mEPSPS) from maize that confers tolerance to glyphosate herbicide in transgenic plants” *Regulatory Toxicology and Pharmacology*, Vol. 54, Issue 2, pp 143-153. Other glyphosate tolerant genes have been created through the introduction of mutations. These include those isolated by Comai and described at U.S. Pat. Nos. 5,094,945, 4,769,061 and 4,535,060. A single mutant has been utilized, as described in 5,310,667 by substituting an alanine residue for a glycine residue at between positions 80 and 120. Double mutants are also described at U.S. Pat. Nos. 6,225,114 and 5,866,775 in which, in addition to the above mutation, a second mutation (a threonine residue for an alanine residue between positions 170 and 210) is introduced into a wild-type EPSPS gene.

Other work resulted in the production of a glyphosate tolerant EPSPS maize through the introduction of a double mutant EPSPS gene bearing mutations at residue 102 (changing threonine to isoleucine) and at residue 106 (changing proline to serine) of the amino acid sequence encoded by GenBank Accession No. X63374 and shown in U.S. Pat. Nos. 6,566,587 and 6,040,497, each of which are incorporated herein by reference in their entirety.

The expression of foreign genes in plants is known to be influenced by their location in the plant genome, perhaps due to chromatin structure (e.g., heterochromatin) or the proximity of transcriptional regulatory elements (e.g., enhancers) close to the integration site (Weising et al. (1988) *Ann. Rev. Genet.* 22: 421-477, 1988). At the same time the presence of the transgene at different locations in the genome influences the overall phenotype of the plant in different ways. For this reason, it is often necessary to screen a large number of events in order to identify an event characterized by optimal expression of an introduced gene of interest. For example, it has been observed in plants and in other organisms that there may be a wide variation in levels of expression of an introduced gene among events. There may also be differences in spatial or temporal patterns of expression, for example, differences in the relative expression of a transgene in various plant tissues, that may not correspond to the patterns expected from transcriptional regulatory elements present in the introduced gene construct. It is also observed that the transgene insertion can affect the endogenous gene expression. For these reasons, it is common to produce hundreds to thousands of different events and screen those events for a single event that has desired transgene expression levels and patterns for commercial purposes. An event that has desired levels or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

SUMMARY OF THE INVENTION

Compositions and methods related to cisgenic glyphosate tolerant maize plants are provided. Specifically, the present invention provides maize plants, plant parts, seeds and commodity products containing the HCEM485 event which imparts tolerance to glyphosate. The maize plant harboring the HCEM485 event at the recited chromosomal location comprises genomic/cisgene HCEM485 junction sequences having at least the polynucleotide sequence of base pairs 367/368 of SEQ ID NO: 4, or which in an embodiment comprises SEQ ID NO: 4, 12, 13, 14, 15, 16, or 17 or fragments thereof sufficient to identify the presence of the HCEM485 event.

Methods and kits for detecting the presence of event HCEM485 are provided, where the presence of a junction region is detected. In one embodiment, a diagnostic amplicon is detected. The methods include use of one or more primers or a specific probe binding to a HCEM485 junction region. Also provided are representative seeds with the American Type culture Collection (ATCC) with Accession No. PTA-12014 and plants, plant cells, plant parts, grain, food and feed and plant products and progeny derived therefrom. Progeny denotes the offspring of any generation of a parent plant comprising the HCEM485 Event. The characterization of the genomic insertion site of event HCEM485 provides for an enhanced breeding efficiency and enables the use of molecular markers to track the insert in the breeding populations and progeny thereof. Various methods and compositions for the identification, detection, and use of the maize event HCEM485 are provided. All references cited herein are incorporated herein by reference in their entirety.

BRIEF DESCRIPTION OF THE DRAWINGS

FIG. 4 shows the amplified nucleotide sequence of SEQ ID NO: 4 obtained using primer 302 (SEQ ID NO: 5). Primer 302 is underlined at the beginning of the sequence, and its complementary region underlined at the end of the sequence (SEQ ID NO: 6). The complementary region to Primer 506 is shown in bold (SEQ ID NO: 11). The junction region at bases 367 and 368 is shown in bold and italics.

DETAILED DESCRIPTION OF THE INVENTION

Figure 1:
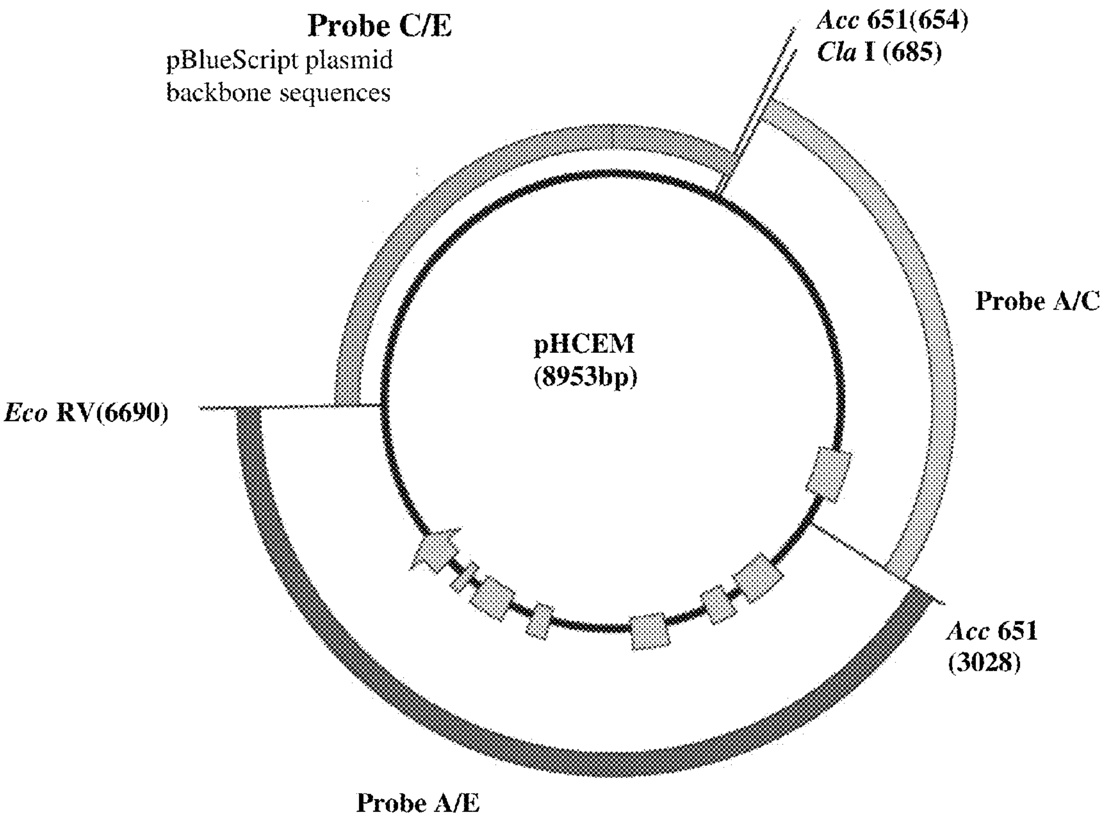
FIG. 1 shows the plasmid map of pHCEM used to produce the HCEM485 maize line.

The invention relates to a novel transformation event of maize plants comprising a transgene/cisgene providing tolerance to exposure to glyphosate herbicide. Compositions and methods related to cisgenicglyphosate-tolerant maize plants are provided. Specifically, the present invention provides maize plants having event HCEM485.

The HCEM event comprises a maize genomic DNA fragment comprising an EPSPS 5' regulatory sequence, and a coding sequence encoding a glyphosate-tolerant EPSPS. The EPSPS 5' regulatory sequence is operably linked to the EPSPS coding sequence. The glyphosate-resistant EPSPS includes a chloroplast transit peptide. The DNA fragment does not contain a non-EPSPS enhancer.

The sequence providing tolerance to glyphosate exposure is described at U.S. Pat. No. 7,045,684 and Reissue No. RE41,943 incorporated herein by reference in its entirety. In U.S. Pat. No. 7,045,684, a genomic EPSPS fragment was isolated from maize as is described in Example 3, incorporated herein by reference in its entirety (SEQ ID NO: 1). The 6.0 kb fragment includes an EPSPS 5' regulatory sequence (the sequence before nucleotide 1868), an EPSPS coding sequence (from nucleotide 1868 to nucleotide 5146), and an EPSPS 3' regulatory sequence (the sequence after nucleotide 5146). The EPSPS coding sequence also encodes a chloroplast transit peptide (from nucleotide 1868 to nucleotide 2041). The sequence encoding this chloroplast transit peptide can be predicted using the computer program PSORT maintained on the public accessible GenomeNet at Kyoto University, Japan. Subsequently two mutations were introduced into the corn wild-type EPSPS gene; the first a cytosine to thymine substitution at nucleotide 2886, and the second a cytosine to thymine substitution at nucleotide 2897 (SEQ ID NO: 2). The mutated gene (referred to as HCEM) encodes mutant protein which is SEQ ID NO: 3 with the residue at position 164 changed from threonine in the wild-type to isoleucine (Thr to Ile) and at position 168 changed from proline to serine (Pro to Ser). The resulting mutated amino acid sequence was glyphosate resistant.

The mutated nucleotide sequence of SEQ ID NO: 2 includes 2mEPSPS, that is, in this instance, the native corn EPSPS promoter, coding regions or exons (containing the two mutations), introns and 3' terminator region. This was introduced into a corn plant as described in Example 4 of the '684 patent, incorporated herein by reference in its entirety, and resulted in event HCEM485 located on chromosome 10. Resistance to glyphosate in regenerants was confirmed by spraying them with glyphosate at commercial rates. Seed from the regenerants segregated 3:1 for resistance as would be expected with Mendelian inheritance of a transgene. Seeds from backcrossed individuals segregated 1:1.

FIG. 4 shows the 1112 base pair amplified nucleotide sequence (SEQ ID NO: 4, referred to also as J4) obtained using the flanking region of the 2mEPSPS insert. The amplified region includes as base pairs 1-25 primer 302 (SEQ ID NO: 5) which is a portion of the 3' fragment of the inserted DNA. The 302 primer was able to amplify the 3' region of the insert. The final 25 base pairs of J4 (underlined in FIG. 4 and which is SEQ ID NO: 6) is the complement to the 302 primer. The first 367 base pairs (SEQ ID NO: 7) of the J4 amplified sequence have 100% homology to the 3' sequence of the HCEM fragment and thus represent this region of the insert. The remaining portion of the sequence, base pairs 368-1112, represent chromosome 10 of the maize genome (SEQ ID NO: 8) with by 368-1092 having 100% homology to chromosome 10 (SEQ ID NO: 9). Thus the junction between the insert and maize genome is base pair 367-368. Primer 506 (SEQ ID NO: 10) can also be used with primer 302, as described below to amplify a fragment. The region complementary to Primer 506 is shown in bold face in FIG. 4 and is SEQ ID NO: 11. The maize plant harboring the HCEM485 event at the recited chromosomal location comprises genomic/inserted DNA junctions having at least the polynucleotide sequence of the junction 367/368. The maize plant harboring the HCEM485 event at the recited chromosomal location comprises genomic/cisgenic HCEM485 junction sequences having at least the polynucleotide sequence of base pairs 367/368 of SEQ ID NO: 4, or which in an embodiment comprises SEQ ID NO: 4, 12, 13, 14 15, 16, or 17 or fragments thereof sufficient to identify the presence of the HCEM485 event. In one embodiment of the invention at least one primer described here produces a diagnostic amplicon that is an amplicon that detects the presence of the HCEM485 event. The amplicon will encompass an amplified product comprising at least one HCEM junction sequence.

The characterization of the genomic insertion site of the HCEM485 event provides for an enhanced breeding efficiency and enables the use of molecular markers to track the insert in the breeding populations and progeny thereof. Various methods and compositions for the identification, detection, and use of the maize HCEM485 event are provided herein. As used herein, the term "event HCEM485 specific" refers to a polynucleotide sequence which is suitable for discriminatively identifying event HCEM485 in plants, plant cells, plant parts, grain, food and feed and plant products and progeny derived therefrom, or in plant materials and plant products such as, but not limited to, food or feed products (fresh or processed) comprising, or derived from plant material. The invention further encompasses a commodity product produced from seed comprising even HCEM485. Such commodity product includes grain, meal, flour, flakes, oil, food or feed products and the like.

Compositions further include seed deposited as Patent Deposit Nos. PTA-12014 and plants, plant cells, and seed derived therefrom. Applicant(s) have made a deposit of at least 2500 seeds of maize event HCEM485 with the American Type Culture Collection (ATCC), Manassas, Va. 20110-2209 USA, on Jul. 29, 2011 and the deposits were assigned ATCC Deposit No. PTA-12014. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C.§112. The seeds deposited with the ATCC on Jul. 29, 2011 were taken from the deposit maintained by Stine Seed, Inc., 22555 Laredo Trail Adel, Iowa 50003. Access to this deposit will be available during the pendency of the application to the Commissioner of Patents and Trademarks and persons determined by the Commissioner to be entitled thereto upon request. Upon allowance of any claims in the application, the Applicant(s) will make available to the public, pursuant to 37 C.F.R. §1.808, sample(s) of the deposit of at least 2500 seeds of hybrid maize B485 with the American Type Culture Collection (ATCC), 10801 University Boulevard, Manassas, Va. 20110-2209. This deposit of seed of maize event HCEM485 will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant(s) have satisfied all the requirements of 37 C.F.R. §§1.801-1.809, including providing an indication of the viability of the sample upon deposit. Applicant(s) have no authority to waive any restrictions imposed by law on the transfer of biological material or its transportation in commerce. Applicant(s) do not waive any infringement of their rights granted under this patent or rights applicable to event HCEM485 under the Plant Variety Protection Act (7 USC §2321 et seq.). Unauthorized seed multiplication prohibited. The seed may be regulated.

As used herein, the term "maize" means any maize plant and includes all plant varieties that can be bred with maize. As used herein, the term plant includes plant cells, plant organs, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise a HCEM485 event.

A transgenic/cisgenic "event" is produced by transformation of plant cells with a heterologous DNA construct(s), including a nucleic acid expression cassette that comprises a transgene of interest, the regeneration of a population of plants resulting from the insertion of the transgene into the genome of the plant, and selection of a particular plant characterized by insertion into a particular genome location. An event is characterized phenotypically by the expression of the transgene(s). When referring here to a transgene of interest is meant to encompass the cisgene of interest, that is, a gene in which the nucleic acid molecules introduced into the plant are sequences found in a wild-type plant, but which have been introduced into the plant by human intervention. The term "event" also refers to progeny produced by a sexual outcross between the transformant and another variety that include the heterologous DNA. Even after repeated back-crossing to a recurrent parent, the inserted DNA and flanking DNA from the transformed parent is present in the progeny of the cross at the same chromosomal location. The term "event" also refers to DNA from the original transformant comprising the inserted DNA and flanking sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

An elite event is one in which the presence of the heterologous DNA does not adversely impact agronomic and other desired characteristics of the plant and which is stably inherited. A plant and plant material may comprise one or more events in its genome.

As used herein, "insert DNA" refers to the heterologous DNA within the expression cassettes used to transform the plant material while "flanking DNA" can comprise either genomic DNA naturally present in an organism such as a plant, or foreign (heterologous) DNA introduced via the transformation process, e.g. fragments associated with the transformation event. A "flanking region" or "flanking sequence" as used herein refers to a sequence of at least 20, 30, 50, 100, 200, 300, 400, 1000, 1500, 2000, 2500, or 5000 base pair or greater or any amount in-between which is located either immediately upstream of and contiguous with or immediately downstream of and contiguous with the original insert DNA molecule. Non-limiting examples of the flanking regions of the HCEM485 event comprise polynucleotide sequences that are set forth in SEQ ID NO: 8 and 9 and variants and fragments thereof.

During the process of introducing an insert into the genome of plant cells, it is not uncommon for some deletions or other alterations of the insert and/or genomic flanking sequences to occur. Thus, the relevant segment of the DNA sequence provided herein might comprise some minor variations. The same is true for the flanking sequences provided herein. Thus, a plant comprising a polynucleotide having some range of identity with the subject flanking and/or insert sequences is within the scope of the subject invention. Identity to the sequence of the present invention can be a polynucleotide sequence having at least 65% sequence identity, more preferably at least 70% sequence identity, more preferably at least 75% sequence identity, more preferably at least 80% identity, and more preferably at least 85% 86%, 87%, 88%, 89%, 90%, 91%, 92%, 93%, 94%, 95%, 96%, 97%, 98%, 99% sequence identity with a sequence exemplified or described herein. Hybridization and hybridization conditions as provided herein can also be used to define such plants and polynucleotide sequences of the subject invention. The sequence which comprises the flanking sequences plus the full insert sequence can be confirmed with reference to the deposited seed.

Transformation procedures leading to random integration of the foreign DNA will result in transformants containing different flanking regions characteristic of and unique for each transformant. A "junction" is a point where two specific DNA fragments join. For example, a junction exists where insert DNA joins flanking DNA. A junction point also exists in a transformed organism where two DNA fragments join together in a manner that is modified from that found in the native organism. As used herein, "junction DNA" refers to DNA that comprises a junction point. Non-limiting examples of junction DNA from the HCEM485 event set are forth in SEQ ID NO: 4, 12, 13, 14, 15, 16 and 17 and variants and fragments thereof. The amplicon produced using these primers in the DNA amplification method is diagnostic for maize event HCEM485.

In an embodiment, a HCEM485 plant can be bred by first sexually crossing a first parental maize plant grown from the HCEM485 maize plant (or progeny thereof derived from transformation with the expression cassettes of the embodiments of the present invention that confer herbicide tolerance) and a second parental maize plant that lacks the herbicide tolerance phenotype, thereby producing a plurality of first progeny plants; and then selecting at least one first progeny plant that displays the desired herbicide tolerance;

and selfing the first progeny plant, thereby producing a plurality of second progeny plants; and then selecting from the second progeny plants which display the desired herbicide tolerance. These steps can further include the back-crossing of the first herbicide tolerant progeny plant or the second herbicide tolerant progeny plant to the second parental maize plant or a third parental maize plant, thereby producing a maize plant that displays the desired herbicide tolerance. It is further recognized that assaying progeny for phenotype is not required. Various methods and compositions, as disclosed elsewhere herein, can be used to detect and/or identify the HCEM485 event.

Two different transgenic plants can also be sexually crossed to produce offspring that contain two independently segregating added, exogenous genes. Selfing of appropriate progeny can produce plants that are homozygous for both added, exogenous genes. Back-crossing to a parental plant and out-crossing with a non-transgenic plant are also contemplated, as is vegetative propagation. Descriptions of other breeding methods that are commonly used for different traits and crops can be found in one of several references, e.g., Poehlman (1995) *Breeding Field Crops*. AVI Publication Co., Westport Conn., 4$^{th}$ Edit. and Fehr (1987), in Breeding Methods for Cultivar Development, Wilcos J. ed., American Society of Agronomy, Madison Wis.

The term "germplasm" refers to an individual, a group of individuals, or a clone representing a genotype, variety, species or culture, or the genetic material thereof. A "line" or "strain" is a group of individuals from a common ancestry. Inbred lines are the product of inbreeding, typically five or more generations of self-pollinations and selection and is a true breeding strain. A "variety" is a subdivision of a species, a group of similar plants that by structural and/or agronomic features can be identified from other varieties within the same species.

Inbred maize lines are typically developed for use in the production of maize hybrids and for use as germplasm in breeding populations for the creation of new and distinct inbred maize lines. Inbred maize lines are often used as targets for the introgression of novel traits through traditional breeding and/or molecular introgression techniques. Inbred maize lines need to be highly homogeneous, homozygous and reproducible to be useful as parents of commercial hybrids. Many analytical methods are available to determine the homozygosity and phenotypic stability of inbred lines. The phrase "hybrid plants" refers to plants which result from a cross between genetically different individuals. The term "crossed" or "cross" in the context of this invention means the fusion of gametes, e.g., via pollination to produce progeny (i.e., cells, seeds, or plants) in the case of plants. The term encompasses both sexual crosses (the pollination of one plant by another) and selfing (self-pollination, i.e., when the pollen and, ovule are from the same plant). The term "introgression" refers to the transmission of a desired allele of a genetic locus from one genetic background to another. In one method, the desired alleles can be introgressed through a sexual cross between two parents, wherein at least one of the parents has the desired allele in its genome.

In some embodiments, the event can be "stacked" with other traits, including, for example, agronomic traits and/or insect-inhibitory proteins and/or resistance to the same or other herbicides. Stacking refers to combining traits into a line. One method is to transform a plant with two or more genes at the same time, or sequentially. A further method is to cross parents having the trait of interest and selecting progeny with the combined traits. Two or more different traits may be combined with such a process. In some embodiments, the polynucleotide conferring the maize HCEM485 event of the invention are engineered into a molecular stack.

In an embodiment, the maize HCEM485 event of the invention comprise one or more traits of interest, and in more specific embodiments, the plant is stacked with any combination of polynucleotide sequences of interest in order to create plants with a desired combination of traits. A trait, as used herein, refers to the phenotype derived from a particular sequence or groups of sequences. Examples, without intending to be limiting, of other traits with which the event can be combined include other herbicide tolerance providing genes, such as combination with other genes encoding glyphosate tolerance, (such as glyphosate oxidase (GOX) or glyphosate acetyl transferase (GAT)); glufosinate tolerance (as through use of the bar or pat gene); acetolactate synthase inhibiting tolerance as with imidazolinones, sulfonylureas, triazolopyrimidine sulfonanilide; bromozynil tolerance; tolerance to inhibitors of HPPD (4-hydroxylphenyl-pyruvate-dioxygenase) enzyme; tolerance to herbicides converted to phenoxyaceate auxin (such as 2,4-D) as with the aad-12 gene and the like. Still further examples include stacking polynucleotides encoding polypeptides having pesticidal and/or insecticidal activity, such as *Bacillus thuringiensis* toxic proteins such as the Cry protein encoding nucleotide genes (such as Cry1A, Cry1A, Cry1F, Cry1C, for example) or vegetative insecticidal proteins (such as VIP3 encoding genes); genes providing stress tolerance, fungal tolerance, or other desirable traits such as increased yield, particular oil profiles and any of a variety of desirable traits. It will be understood by one skilled in the art that such traits for combination can be the result of a molecular stack by combining with other transgenes, or combining with other nontransgenic traits.

These stacked combinations can be created by any method including, but not limited to, breeding plants by any conventional methodology, or genetic transformation. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes or contained on the same transformation cassette. Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. A multitude of methods for site specific recombination are available to one skilled in the art, including, by way of example without limitation, introducing FRT sites in the FLP/FRT system and/or Lox sites that may be used in the Cre/Lox system. For example, see Lyznik, et al., (2003) "Site-Specific Recombination for Genetic Engineering in Plants," *Plant Cell Rep* 21:925-932.

Deoxyribonucleic acid (DNA) is a polymer comprising four mononucleotide units, (D)dAMP (2'-(D) deoxyadenosine-5-monophosphate), dGMP (2'-(D)deoxyguanosine-5-monophosphate), dCMP (2'-(D)deoxycytosine-5-monophosphate) and dTMP (2'-(D)deoxycytosine-5-monophosphate) linked in various sequences by 3',5'-phosphodiester bridges. The structural DNA consists of multiple nucleotide triplets called "codons" which code for the amino acids. The codons correspond to the various amino acids as follows: Arg (CGA, CGC, CGG, CGT, AGA, AGG); Leu (CTA, CTC, CTG, CTT, TTA, TTG); Ser (TCA, TCC, TCG, TCT, AGC, AGT); Thr (ACA, ACC, ACG, ACT); Pro (CCA, CCC, CCG, CCT); Ala (GCA, GCC, GCG, GCT); Gly (GGA, GGC, GGG, GGT); Ile (ATA, ATC, ATT); Val (GTA, GTC, GTG, GTT); Lys (AAA, AAG); Asn (AAC, AAT); Gln (GAA, CAG); His (CAC, CAT); Glu (GAA, GAG); Asp (GAC, GAT); Tyr (TAC, TAT); Cys (TGC, TGT); Phe (TTC, TTT); Met (ATG); and Trp (UGG). Moreover, due to the redundancy of the genetic code (i.e., more than one codon for all but two amino acids), there are many possible DNA sequences which may code for a particular amino acid sequence.

As used herein, the use of the term "polynucleotide" is not intended to limit the present invention to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like. Unless otherwise indicated, a particular nucleic acid sequence also implicitly encompasses conservatively modified variants thereof (e.g. degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) *Nucleic Acid Res.* 19:5081; Ohtsuka et al. (1985) *J. Biol. Chem.* 260:2605-2608; Rossolini et al. (1994) *Mol. Cell. Probes* 8:91-98). The term nucleic acid is used interchangeably with gene, cDNA, and mRNA encoded by a gene.

A HCEM485 plant comprises an expression cassette having a sequence encoding a mutant EPSPS that provides tolerance to exposure to glyphosate, the EPSPS 5' regulatory sequence and chloroplast transit peptide.

The term introduced in the context of inserting a nucleic acid into a cell, includes transfection or transformation or transduction and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA). When referring to introduction of a nucleotide sequence into a plant is meant to include transformation into the cell, as well as crossing a plant having the sequence with another plant, so that the second plant contains the heterologous sequence, as in conventional plant breeding techniques. Such breeding techniques are well known to one skilled in the art. For a discussion of plant breeding techniques, see Poehlman (1995) supra. Backcrossing methods may be used to introduce a gene into the plants. This technique has been used for decades to introduce traits into a plant. An example of a description of this and other plant breeding methodologies that are well known can be found in references such as Poehlman, supra, and *Plant Breeding Methodology*, edit. Neal Jensen, John Wiley & Sons, Inc. (1988). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred gene from the nonrecurrent parent.

In specific embodiments, the polynucleotides of the invention comprise the junction DNA sequence set forth in SEQ ID NO: 4, 12, 13, 14, 15, 16, or 17 or variants and fragments thereof. In specific embodiments, methods of detection described herein amplify a polynucleotide comprising the junction of the HCEM485 specific event. Fragments and variants of junction DNA sequences are suitable for discriminatively identifying event HCEM485. As discussed elsewhere herein, such sequences find use as primers and/or probes.

In other embodiments, the polynucleotides of the invention comprise polynucleotides that can detect a HCEM485 event or a HCEM485 specific region. Such sequences include any polynucleotide set forth in SEQ ID NOS: 1, 2, 3, 4, 5, 6, 7, 8, 9, 10, 11, 12, 13, 14, 15, 16, 17, 18, 19, 20, 21, or 22 or variants and fragments thereof. Fragments and variants of polynucleotides that detect a HCEM485 event or a HCEM485 specific region are suitable for discriminatively identifying event HCEM485. As discussed elsewhere herein, such sequences find use as primers and/or probes. In one embodiment further provided are isolated DNA nucleotide primer sequences or kits comprising or consisting of a sequence set forth in SEQ ID NO: 5, 6, 10, 11, 18, 19, or 20 or a complement thereof.

"Variants" is intended to mean substantially similar sequences. For polynucleotides, a variant comprises a polynucleotide having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide.

It is to be understood that as used herein the term "transgenic/cisgenic" includes any cell, cell line, callus, tissue, plant part, or plant, the genotype of which has been altered by the presence of a heterologous nucleic acid including those transgenics initially so altered as well as those created by sexual crosses or asexual propagation from the initial transgenic/cisgenic.

Various methods and compositions for identifying event HCEM485 are provided. Such methods find use in identifying and/or detecting a HCEM485 event in any biological material. Such methods include, for example, methods to confirm seed purity and methods for screening seeds in a seed lot for a HCEM485 event. In one embodiment, a method for identifying event HCEM485 in a biological sample is provided and comprises contacting the sample with a primer or a first and a second primer; and, amplifying a polynucleotide comprising a HCEM485 specific region (a region within the flanking region of the event and preferably also comprising part of the insert DNA contiguous therewith).

A biological sample can comprise any sample in which one desires to determine if DNA having event HCEM485 is present. For example, a biological sample can comprise any plant material or material comprising or derived from a plant material such as, but not limited to, food or feed products. As used herein, "plant material" refers to material which is obtained or derived from a plant or plant part. In specific embodiments, the biological sample comprises a maize tissue.

The nucleotide sequences of the invention can also be used as molecular markers such as RFLP, AFLP, RAPD markers, SNPs and SSRs to identify the herbicide resistance trait where a plant is progeny of a parent having the HCEM485 Event.

Thus, in one specific embodiment, a method of detecting the presence of maize event HCEM485 or progeny thereof in a biological sample is provided. The method comprises (a) extracting a DNA sample from the biological sample; (b) providing a primer or pair of DNA primer molecules, including, but not limited to, any combination of sequences in SEQ ID NO: 5, 6, 10, 11, 18 and 19 or a complement thereof (c) providing DNA amplification reaction conditions; (d) performing the DNA amplification reaction, thereby producing a DNA amplicon molecule; and (e) detecting the DNA amplicon molecule, wherein the detection of said DNA amplicon molecule in the DNA amplification reaction indicates the presence of maize event HCEM485. In order for a nucleic acid molecule to serve as a primer or probe it needs only be sufficiently complementary in sequence to be able to form a stable double-stranded structure under the particular solvent and salt concentrations employed.

A polynucleotide is said to be the "complement" of another polynucleotide if they exhibit complementarity. As used herein, molecules are said to exhibit "complete complementarity" when every nucleotide of one of the polynucleotide molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions.

Further provided are methods of detecting the presence of DNA corresponding to the HCEM485 event in a sample. In one embodiment, the method comprises (a) contacting the biological sample with a polynucleotide probe that hybridizes under stringent hybridization conditions with DNA from maize event HCEM485 and specifically detects the HCEM485 event; (b) subjecting the sample and probe to stringent hybridization conditions; and (c) detecting hybridization of the probe to the DNA, wherein detection of hybridization indicates the presence of the HCEM485 event.

Methods for preparing and using probes and primers are described, for example, in *Molecular Cloning: A Laboratory Manual,* 2nd ed, vol. 1-3, ed. Sambrook et al., Cold Spring Harbor Laboratory Press, Cold Spring Harbor, N.Y. 1989; *Current Protocols in Molecular Biology*, ed. Ausubel et al., Greene Publishing and Wiley-Interscience, New York, 1992 (with periodic updates); and Innis et al., *PCR Protocols: A Guide to Methods and Applications*, Academic Press: San Diego, 1990. PCR primer pairs can be derived from a known sequence, for example, by using computer programs intended for that purpose such as the PCR primer analysis tool in Vector NTI version 6 (Informax Inc., Bethesda Md.); PrimerSelect (DNASTAR Inc., Madison, Wis.); and Primer (Version 0.5 1991, Whitehead Institute for Biomedical Research, Cambridge, Mass.). Additionally, the sequence can be visually scanned and primers manually identified using guidelines known to one of skill in the art.

As used herein, a "probe" is an isolated polynucleotide to which is attached a conventional detectable label or reporter molecule, e.g., a radioactive isotope, ligand, chemiluminescent agent, enzyme, etc. Such a probe is complementary to a strand of a target polynucleotide, in the case of the present invention, to a strand of isolated DNA from maize event HCEM485 whether from a maize plant or from a sample that includes DNA from the event. Probes according to the present invention include not only deoxyribonucleic or ribonucleic acids but also polyamides and other probe materials that can specifically detect the presence of the target DNA sequence.

As used herein, "primers" are isolated polynucleotides that are annealed to a complementary target DNA strand by nucleic acid hybridization to form a hybrid between the primer and the target DNA strand, then extended along the target DNA strand by a polymerase, e.g., a DNA polymerase. Primers and primer pairs of the invention refer to their use for amplification of a target polynucleotide, e.g., by the polymerase chain reaction (PCR) or other conventional nucleic-acid amplification methods. "PCR" or "polymerase chain reaction" is a technique used for the amplification of specific DNA segments (see, U.S. Pat. Nos. 4,683,195 and 4,800,159; herein incorporated by reference). Any combination of primers (i.e., SEQ ID NO: 5, 6 10, 11, 18 or 19) disclosed herein can be used such that the pair allows for the detection of a HCEM485 event or specific region. Primer 302 (SEQ ID NO: 5) may be used alone, and in a preferred embodiment, is used with low stringent conditions. Non-limiting examples of primer pairs include SEQ ID NOS: 5 and 10 and SEQ ID NOS: 18 and 19.

Probes and primers are of sufficient nucleotide length to bind to the target DNA sequence and specifically detect and/or identify a polynucleotide having a HCEM485 event. It is recognized that the hybridization conditions or reaction conditions can be determined by the operator to achieve this result. This length may be of any length that is of sufficient length to be useful in a detection method of choice. Generally, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 polynucleotides or more in length. Such probes and primers can hybridize specifically to a target sequence under high stringency hybridization conditions. Probes and primers according to embodiments of the present invention may have complete DNA sequence identity of contiguous nucleotides with the target sequence, although probes differing from the target DNA sequence and that retain the ability to specifically detect and/or identify a target DNA sequence may be designed by conventional methods. Accordingly, probes and primers can share about 80%, 81%, 82%, 83%, 84%, 85%, 86%, 87%, 88%, 89%, 90%, 91%, 92%, 93%, 94%, 95%, 96%, 97%, 98%, 99% or greater sequence identity or complementarity to the target polynucleotide (i.e., SEQ ID NO: 1-20), or can differ from the target sequence by 1, 2, 3, 4, 5, 6 or more nucleotides. Probes can be used as primers, but are generally designed to bind to the target DNA or RNA and are not used in an amplification process. In one non-limiting embodiment, a probe can comprises a polynucleotide encoding the HCEM sequence or any variant or fragment of these sequences.

Any primer can be employed in the methods of the invention that allows a HCEM485 specific region to be amplified and/or detected. In an embodiment the primer comprises the sequence of or a fragment of a polynucleotide of SEQ ID NO: 2, 4, or 7 and shares sufficient sequence identity or complementarity to the polynucleotide to amplify the HCEM485 specific region. For example, Primer 302, SEQ ID NO: 5 may be used alone under low stringent conditions. In another embodiment a primer pair can be used which can comprise the sequence of or a fragment of SEQ ID NO: 2, 5 or 7 and the sequence of or a fragment or variant of SEQ ID NO: 8 or 9.

In still further embodiments, the first and the second primer can comprise any one or any combination of the sequences set forth in SEQ ID NO: 5, 6, 10, 11, 18 or 19. The primers can be of any length sufficient to amplify a HCEM485 specific region including, for example, at least 6, 7, 8, 9, 10, 15, 20, 15, or 30 or about 7-10, 10-15, 15-20, 20-25, 25-30, 30-35, 35-40, 40-45 nucleotides or longer.

Specific primers can be used to amplify an integration fragment to produce an amplicon that can be used as a "specific probe" or can itself be detected for identifying event HCEM485 in biological samples. Alternatively, a probe of the invention can be used during the PCR reaction to allow for the detection of the amplification event (i.e., a TaqMan® probe or an MGB probe, so called real-time PCR). When the probe is hybridized with the polynucleotides of a biological sample under conditions which allow for the binding of the probe to the sample, this binding can be detected and thus allow for an indication of the presence of event HCEM485 in the biological sample. Such identification of a bound probe has been described in the art. In an embodiment of the invention, the specific probe is a sequence which, under optimized conditions, hybridizes specifically to a region within the 5' or 3' flanking region of the event and also comprises a part of the foreign DNA contiguous therewith. The specific probe may comprise a sequence of at least 80%, between 80 and 85%, between 85 and 90%, between 90 and 95%, and between 95 and 100% identical (or complementary) to a specific region of the HCEM485 event.

Any of the polynucleotides and fragments and variants thereof employed in the methods and compositions of the invention can share sequence identity to a region of the transgene insert of the HCEM485 event, a junction sequence of the HCEM485 event or a flanking sequence of the HCEM485 event. Methods to determine the relationship of various sequences are known. As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence. As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Optimal alignment of sequences for comparison can use any means to analyze sequence identity (homology) known in the art, e.g., by the progressive alignment method of termed "PILEUP" (Morrison, *Mol. Biol. Evol.* 14:428-441 (1997), as an example of the use of PILEUP); by the local homology algorithm of Smith & Waterman (*Adv. Appl. Math.* 2: 482 (1981)); by the homology alignment algorithm of Needleman & Wunsch (*J. Mol. Biol.* 48:443 (1970)); by the search for similarity method of Pearson (*Proc. Natl. Acad. Sci. USA* 85: 2444 (1988)); by computerized implementations of these algorithms (e.g., GAP, BEST FIT, FASTA, and TFASTA in the Wisconsin Genetics Software Package, Genetics Computer Group, 575 Science Dr., Madison, Wis.); ClustalW (CLUSTAL in the PC/Gene program by Intelligenetics, Mountain View, Calif., described by, e.g., Higgins, *Gene* 73: 237-244 (1988); Corpet, *Nucleic Acids Res.* 16:10881-10890 (1988); Huang, *Computer Applications in the Biosciences* 8:155-165 (1992); and Pearson, *Methods in Mol. Biol.* 24:307-331 (1994); Pfam (Sonnhammer, *Nucleic Acids Res.* 26:322-325 (1998); TreeAlign (Hein, *Methods Mol. Biol.* 25:349-364 (1994); MEG-ALIGN, and SAM sequence alignment computer programs; or, by manual visual inspection.

Another example of algorithm that is suitable for determining sequence similarity is the BLAST algorithm, which is described in Altschul et al, *J. Mol. Biol.* 215: 403-410 (1990). The BLAST programs (Basic Local Alignment Search Tool) of Altschul, S. F., et al., (1993) *J. Mol. Biol.* 215:403-410) searches under default parameters for identity to sequences contained in the BLAST "GENEMBL" database. A sequence can be analyzed for identity to all publicly available DNA sequences contained in the GENEMBL database using the BLASTN algorithm under the default parameters.

Software for performing BLAST analyses is publicly available through the National. Center for Biotechnology Information, world wide web ncbi.nlm.nih.gov/; see also Zhang, *Genome Res.* 7:649-656 (1997) for the "Power-BLAST" variation. This algorithm involves first identifying high scoring sequence pairs (HSPs) by identifying short words of length W in the query sequence that either match or satisfy some positive valued threshold score T when aligned with a word of the same length in a database sequence. T is referred to as the neighborhood word score threshold (Altschul et al, *J. Mol. Biol.* 215: 403-410 (1990)). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a wordlength (W) of 11, the BLOSUM62 scoring matrix (see Henikoff, *Proc. Natl. Acad. Sci. USA* 89:10915-10919 (1992)) alignments (B) of 50, expectation (E) of 10, M=5, N=−4, and a comparison of both strands. The term BLAST refers to the BLAST algorithm which performs a statistical analysis of the similarity between two sequences; see, e.g., Karlin, *Proc. Natl. Acad. Sci. USA* 90:5873-5787 (1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

In an embodiment, GAP (Global Alignment Program) can be used. GAP uses the algorithm of Needleman and Wunsch *J. Mol. Biol.* 48:443-453 (1970) to find the alignment of two complete sequences that maximizes the number of matches and minimizes the number of gaps. Default gap creation penalty values and gap extension penalty values in the commonly used Version 10 of the Wisconsin Package® (Accelrys, Inc., San Diego, Calif.) for protein sequences are 8 and 2, respectively. For nucleotide sequences the default gap creation penalty is 50 while the default gap extension penalty is 3. Percent Similarity is the percent of the symbols that are similar. Symbols that are across from gaps are ignored. A similarity is scored when the scoring matrix value for a pair of symbols is greater than or equal to 0.50, the similarity threshold. A general purpose scoring system is the BLOSUM62 matrix (Henikoff and Henikoff, *Proteins,* 17: 49-61 (1993)), which is currently the default choice for BLAST programs. BLOSUM62 uses a combination of three matrices to cover all contingencies. Altschul, J. Mol. Biol. 36: 290-300 (1993), herein incorporated by reference in its entirety and is the scoring matrix used in Version 10 of the Wisconsin Package® (Accelrys, Inc., San Diego, Calif.) (see Henikoff & Henikoff (1989) *Proc. Natl. Acad. Sci. USA* 89:10915).

As used herein, "sequence identity" or "identity" in the context of two nucleic acid sequences makes reference to the residues in the two sequences that are the same when aligned for maximum correspondence over a specified comparison window.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison, and multiplying the result by 100 to yield the percentage of sequence identity.

As used herein, "amplified DNA" or "amplicon" refers to the product of polynucleotide amplification of a target polynucleotide that is part of a nucleic acid template. For example, to determine whether a maize plant resulting from a sexual cross contains the HCEM485 event, DNA extracted from the maize plant tissue sample may be subjected to a polynucleotide amplification method using a primer diagnostic for a HCEM485 or a primer pair that includes a first primer derived from flanking sequence adjacent to the insertion site of inserted heterologous DNA, and a second primer derived from the inserted heterologous DNA to produce an amplicon that is diagnostic for the presence of the HCEM485 event DNA. In specific embodiments, the amplicon comprises a HCEM485 junction polynucleotide (i.e., SEQ ID NO: 4, 12, 13, 14, 15, 16, or 17). By "diagnostic" for a HCEM485 event the use of any method or assay which discriminates between the presence or the absence of a HCEM485 event in a biological sample is intended. Alternatively, the second primer may be derived from the flanking sequence. In still other embodiments, primer pairs can be derived from flanking sequence on both sides of the inserted DNA so as to produce an amplicon that includes the entire insert polynucleotide of the expression construct as well as the sequence flanking the transgenic insert. The amplicon is of a length and has a sequence that is also diagnostic for the event (i.e., has a junction DNA from a HCEM485 event). The amplicon may range in length from the combined length of the primer pairs plus one nucleotide base pair to any length of amplicon producible by a DNA amplification protocol. A member of a primer pair derived from the flanking sequence may be located a distance from the inserted DNA sequence, this distance can range from one nucleotide base pair up to the limits of the amplification reaction, or about twenty thousand nucleotide base pairs. The use of the term "amplicon" specifically excludes primer dimers that may be formed in the DNA thermal amplification reaction.

Primers and probes based on the flanking DNA and insert sequences disclosed herein can be used to confirm the disclosed sequences by conventional methods, e.g., by recloning and sequencing such sequences. The polynucleotide probes and primers of the present invention specifically detect a target DNA sequence. Any conventional nucleic acid hybridization or amplification method can be used to identify the presence of DNA from a transgenic event in a sample. By "specifically detect" it is intended that the polynucleotide can be used either as a primer to amplify a HCEM485 specific region or the polynucleotide can be used as a probe that hybridizes under stringent conditions to a polynucleotide from a HCEM485 event. The level or degree of hybridization which allows for the specific detection of a HCEM485 event or a specific region of a HCEM485 event is sufficient to distinguish the polynucleotide with the HCEM485 specific region from a polynucleotide lacking this region and thereby allow for discriminately identifying a HCEM485 event. By "sharing sufficient sequence identity or complementarity to allow for the amplification of a HCEM485 specific event" is intended the sequence shares at least 80%, 81%, 82%, 83%, 84%, 85%, 86%, 87%, 88%, 89%, 90%, 91%, 92%, 93%, 94%, 95%, 96%, 97%, 98%, 99% or 100% identity or complementarity to a fragment or across the full length of the polynucleotide from the HCEM485 specific region.

Regarding the amplification of a target polynucleotide (e.g., by PCR) using a particular amplification primer pair, "stringent conditions" are conditions that permit the primer pair to hybridize to the target polynucleotide to which one primer having the corresponding wild-type sequence (or its complement) and another primer having the corresponding HCEM485 inserted DNA sequence would bind and preferably to produce an identifiable amplification product (the amplicon) having a HCEM485 specific region in a DNA thermal amplification reaction. In a PCR approach, oligonucleotide primers can be designed for use in PCR reactions to amplify a HCEM485 specific region. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) PCR Methods Manual (Academic Press, New York). Methods of amplification are further described in U.S. Pat. Nos. 4,683,195, 4,683,202 and Chen et al. (1994) PNAS 91:5695-5699. These methods as well as other methods known in the art of DNA amplification may be used in the practice of the embodiments of the present invention. It is understood that a number of parameters in a specific PCR protocol may need to be adjusted to specific laboratory conditions and may be slightly modified and yet allow for the collection of similar results. These adjustments will be apparent to a person skilled in the art.

The amplified polynucleotide (amplicon) can be of any length that allows for the detection of the HCEM485 event or a HCEM485 specific region. For example, the amplicon can be about 10, 50, 100, 200, 300, 500, 700, 100, 2000, 3000, 4000, 5000 nucleotides in length or longer. In specific embodiments, the specific region of the HCEM485 event is detected.

As discussed elsewhere herein, any method to amplify the HCEM485 event or specific region can be employed, including for example, Polymerase Chain Reaction (PCR) or real time PCR (RT-PCR). See, for example, Livak et al. (1995a) "Oligonucleotides with fluorescent dyes at opposite ends provide a quenched probe system for detecting PCR product and nucleic acid hybridization" *PCR methods and Application.* 4:357-362; U.S. Pat. No. 5,538,848; U.S. Pat. No. 5,723,591; Applied Biosystems User Bulletin No. 2, "Relative Quantitation of Gene Expression," P/N 4303859; and, Applied Biosystems User Bulletin No. 5, "Multiplex PCR with TaqMan® VIC probes," P/N 4306236.

In hybridization techniques, all or part of a polynucleotide that selectively hybridizes to a target polynucleotide having a HCEM485 specific event is employed. By "stringent conditions" or "stringent hybridization conditions" when referring to a polynucleotide probe conditions under which a probe will hybridize to its target sequence to a detectably greater degree than to other sequences (e.g., at least 2-fold over background) are intended. Regarding the amplification of a target polynucleotide (e.g., by PCR) using a particular amplification primer or a primer pair, "stringent conditions" are conditions that permit the primer or primer pair to hybridize to the target polynucleotide to amplify the HCEM 3' region and chromosome 10 region, or, with a primer pair, in which one primer having the corresponding wild-type sequence and another primer having the corresponding HCEM485 inserted 3' DNA sequence. Stringent conditions are sequence-dependent and will be variable in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of identity are detected (heterologous probing). Generally, a probe is less than about 1000 nucleotides in length or less than 500 nucleotides in length.

As used herein, a substantially identical or complementary sequence is a polynucleotide that will specifically hybridize to the complement of the nucleic acid molecule to which it is being compared under high stringency conditions. One skilled in the art can use a variety of conditions of hybridization to achieve different degrees of selectivity toward the target sequence. See e.g., *Current Protocols in Molecular Biology*, John Wiley & Sons, N.Y. (1989), 6.3.1-6.3.6. Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 50° C. Exemplary high stringency conditions include hybridization in 50% formamide, 1 M NaCl, 0.1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.,* 138:267-284 (1984): $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of the complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with 90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen (1993) *Laboratory Techniques in Biochemistry and Molecular Biology*—Hybridization with Nucleic Acid Probes, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.) and Haymes et al. (1985) In: *Nucleic Acid Hybridization*, a Practical Approach, IRL Press, Washington, D.C.

Various methods can be used to detect the HCEM485 specific region or amplicon thereof, including, but not limited to, Genetic Bit Analysis (Nikiforov et al. (1994) *Nucleic Acid Res.* 22: 4167-4175) where a DNA oligonucleotide is designed which overlaps both the adjacent flanking DNA sequence and the inserted DNA sequence. The oligonucleotide is immobilized in wells of a microwell plate. Following PCR of the region of interest (using one primer in the inserted sequence and one in the adjacent flanking sequence) a single-stranded PCR product can be annealed to the immobilized oligonucleotide and serve as a template for a single base extension reaction using a DNA polymerase and labeled ddNTPs specific for the expected next base. Readout may be fluorescent or ELISA-based. A signal indicates presence of the insert/flanking sequence due to successful amplification, hybridization, and single base extension.

Another detection method is the Pyrosequencing technique as described by Winge (2000) "Pyrosequencing—a new approach to DNA analysis" *Innov. Pharma. Tech.* 00: 18-24. In this method, an oligonucleotide is designed that overlaps the adjacent DNA and insert DNA junction. The oligonucleotide is annealed to a single-stranded PCR product from the region of interest (one primer in the inserted sequence and one in the flanking sequence) and incubated in the presence of a DNA polymerase, ATP, sulfurylase, luciferase, apyrase, adenosine 5' phosphosulfate and luciferin. dNTPs are added individually and the incorporation results in a light signal which is measured. A light signal indicates the presence of the insert/flanking sequence due to successful amplification, hybridization, and single or multi-base extension.

Fluorescence Polarization as described by Chen et al. ((1999) *Genome Res.* 9: 492-498) is also a method that can be used to detect an amplicon of the invention. Using this method, an oligonucleotide is designed which overlaps the flanking and inserted DNA junction. The oligonucleotide is hybridized to a single-stranded PCR product from the region of interest (one primer in the inserted DNA and one in the flanking DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the insert/flanking sequence due to successful amplification, hybridization, and single base extension.

TaqMan® (PE Applied Biosystems, Foster City, Calif.) is described as a method of detecting and quantifying the presence of a DNA sequence and is fully understood in the instructions provided by the manufacturer. Briefly, a FRET oligonucleotide probe is designed which overlaps the flanking and insert DNA junction. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/insert sequence due to successful amplification and hybridization.

Molecular Beacons have been described for use in sequence detection as described in Tyangi et al. (1996) *Nature Biotech.* 14: 303-308. Briefly, a FRET oligonucleotide probe is designed that overlaps the flanking and insert DNA junction. The unique structure of the FRET probe results in it containing secondary structure that keeps the fluorescent and quenching moieties in close proximity. The FRET probe and PCR primers (one primer in the insert DNA sequence and one in the flanking sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking/insert sequence due to successful amplification and hybridization.

A hybridization reaction using a probe specific to a sequence found within the amplicon is yet another method used to detect the amplicon produced by a PCR reaction.

As used herein, "kit" refers to a set of reagents for the purpose of performing the method embodiments of the invention, more particularly, the identification and/or the detection of the HCEM485 event in biological samples. The kit of the invention can be used, and its components can be specifically adjusted, for purposes of quality control (e.g. purity of seed lots), detection of event HCEM485 in plant material, or material comprising or derived from plant material, such as but not limited to food or feed products.

In specific embodiments, a kit for identifying event HCEM485 in a biological sample is provided. The kit comprises a primer or a primer pair of a first and a second primer, wherein the primer or first and second primer amplify a polynucleotide comprising a HCEM485 specific region. In further embodiments, the kit also comprises a polynucleotide for the detection of the HCEM485 specific region. The kit can comprise, for example, a primer comprising SEQ ID NO: 5 (which functions as both forward and reverse primer and can be used alone, in a preferred embodiment, under low stringency conditions); or a primer pair, the first primer comprising a sequence of or a fragment of a polynucleotide of SEQ ID NO: 2, 4 or 7, wherein the first or the second primer shares sufficient sequence homology or complementarity to the polynucleotide to amplify said HCEM485 specific region. For example, in specific embodiments, the first primer comprises a fragment of a polynucleotide of SEQ ID NO: 2, 7, 8, or 9, wherein the first or the second primer shares sufficient sequence homology or complementarity to the polynucleotide to amplify the HCEM485 specific region. The fragment can comprise 10, 20, 30, 40, 50, 60, 70, or greater consecutive nucleotides. In still further embodiments, the first and the second primer can comprise any one or any combination of the sequences set forth in SEQ ID NO: 5, 6, 10, 11, 18 or 19. The primers can be of any length sufficient to amplify the HCEM485 region including, for example, at least 6, 7, 8, 9, 10, 15, 20, 15, or 30 or about 7-10, 10-15, 15-20, 20-25, 25-30, 30-35, 35-40, 40-45 nucleotides or longer. In other embodiments, SEQ ID NO: 7 or a fragment thereof or any region of SEQ ID NO: 2 can be used as a probe. Such fragments can be used as a probe having at least 10, 20, 30, 40, 50, 60, 70, 80, 90, 100, 110, 120, 130, 140, 150, 160, or 170 or greater consecutive nucleotides of SEQ ID NO:7.

Further provided are DNA detection kits. A detection kit can, for example, include probes and/or primers directed to and/or which comprise junction sequences. Such primers are typically at least about 10 or 15 nucleotides ore more in length. An embodiment provides for nucleotide sequence comprising at least about 10 or 15 nucleotides of a portion of the insert, or complements thereof, and a similar length of the flanking genomic DNA or complements thereof. As noted, the invention includes a primer which is capable of providing amplification of a sequence which identifies the presence of the HCEM event, such as Primer 302 (SEQ ID NO: 5). Another option is to have a primer pair, where one primer hybridizes in the flanking region and one primer hybridizes in the insert. One skilled in the art appreciates that the primer or probe may not be perfectly complementary to the sequence yet be readily employed in the invention. A degree of mismatch may be tolerated as long as they are diagnostic for the event. By way of example, without limitation, with a 20 nucleotide primer, hybridization may yet occur when one or two nucleotides do not bind with the opposite strand, if the base is internal or on the end of the primer opposite the amplicon. In an embodiment, the kit comprises at least one polynucleotide that can specifically detect a HCEM485 specific region or insert DNA, wherein said polynucleotide comprises at least one DNA molecule of a sufficient length of contiguous nucleotides homologous or complementary to SEQ ID NO: 2, 4 or 7, and in another comprises at least one polynucleotide that can specifically detect a maize chromosome 10 region, wherein said polynucleotide comprises at least one DNA molecule of a sufficient length of contiguous nucleotides homologous or complementary to SEQ ID NO: 8 or 9. In specific embodiments, the DNA detection kit comprises a polynucleotide having SEQ ID NO: 4, 12, 13, 14, 15, 16, or 17 and/or comprises a sequence which hybridizes with sequences selected from the group consisting of SEQ ID NO: 8 or 9. In an embodiment of the invention, a kit can comprise the 302 primer (SEQ ID NO: 5) and may comprise a primer pair selected from the group consisting of SEQ ID NO: 5, 6, 10, 11, 18 and 19. In an embodiment the kit may comprise SEQ ID NO: 5 and 10. In another embodiment the kit may comprise SEQ ID NO: 18 and 19 and may include SEQ ID NO: 20.

Zygosity of a plant comprising the event can also be determined using the primers described here. Two primers recognizing the wild-type locus before integration are designed in such a way that they are directed towards each other and have the insertion site located in between the primers. These primers may be primers specifically recognizing flanking sequences. Together with a primer complementary to transforming DNA allow simultaneous diagnostic PCR amplification of the HCEM485 specific locus, as well as of the wild type locus. If the plant is homozygous for the transgenic/cisgenic locus or the corresponding wild type locus, the diagnostic PCR will give rise to a single PCR product typical, preferably typical in length, for either the transgenic or wild type locus. If the plant is hemizygous for the transgenic locus, two locus-specific PCR products will appear, reflecting both the amplification of the transgenic/cisgenic and wild type locus.

Plants comprising the HCEM event have as a characteristic tolerance to application of glyphosate (N-phosphonomethylglycine). When referring to glyphosate, the term should be considered to include any herbicidally effective form of N-phosphonomethylglycine and any salt thereof and forms which result in the production of the glyphosate zwitterion in planta. Glyphosate is a competitive inhibitors of 5-enolpyruvylshikimate-3-phosphate synthase (EC 2.5.1.19) or EPSPS with respect to the binding of PEP (phosphoenolpyruvate). After the application of phosponomethylglycine herbicide to the plant, it is translocated in the plant where it accumulates in the rapidly growing parts, in particular the cauline and root apices, causing damage to the point of destruction of sensitive plants. Depending upon the application rate of the herbicide, the sensitive plant growth is inhibited, that is, its growth is slowed or stopped completely. When referring to resistance or tolerance to the glyphosate herbicide, it is meant that any impact of the herbicide on the plant does not kill the plant; there can be minimal impact on the plant or no impact at all, such that any adverse impact on the plant comprising the inserted nucleic acid molecule providing resistance or tolerance is less than in a plant not comprising a nucleic acid molecule providing resistance or tolerance to glyphosate.

The present invention provides methods for controlling weeds in an area of cultivation, preventing the development or the appearance of herbicide resistant weeds in an area of cultivation, producing a crop, and increasing crop safety. The term “controlling,” and derivations thereof, for example, as in “controlling weeds” refers to one or more of inhibiting the growth, germination, reproduction, and/or proliferation of, and/or killing, removing, destroying, or otherwise diminishing the occurrence and/or activity of a weed. As used herein, an “area of cultivation” comprises any region in which one desires to grow a plant. Such areas of cultivations include, but are not limited to, a field in which a plant is cultivated (such as a crop field, a sod field, a tree field, a managed forest, a field for culturing fruits and vegetables, etc), a greenhouse, a growth chamber, etc.

The methods of the invention comprise planting the area of cultivation with the maize HCEM485 seeds or plants, and in specific embodiments, applying to the crop, seed, weed or area of cultivation thereof an effective amount of a glyphosate composition and, where applicable, another herbicide or chemical of interest either at the same time or at separate times. It is recognized that the herbicide can be applied before or after the crop is planted in the area of cultivation. Such herbicide applications can include an application of glyphosate, any other applicable chemical, or any combination thereof.

In another embodiment, the method of controlling weeds comprises planting the area with a HCEM485 maize crop seed or plant and applying to the crop, crop part, seed of said crop or the area under cultivation, an effective amount of a herbicide, wherein said effective amount comprises a level that is above the recommended label use rate for the crop, wherein said effective amount is tolerated when applied to the HCEM485 maize crop, crop part, seed, or the area of cultivation thereof.

A "control" or "control plant" or "control plant cell" provides a reference point for measuring changes in phenotype of the subject plant or plant cell, and may be any suitable plant or plant cell. A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell which is genetically identical to the subject plant or plant cell but which is not exposed to the same treatment (e.g., herbicide treatment) as the subject plant or plant cell; (e) the subject plant or plant cell itself, under conditions in which the gene of interest is not expressed; or (f) the subject plant or plant cell itself, under conditions in which it has not been exposed to a particular treatment such as, for example, a herbicide or combination of herbicides and/or other chemicals. In some instances, an appropriate control plant or control plant cell may have a different genotype from the subject plant or plant cell but may share the herbicide-sensitive characteristics of the starting material for the genetic alteration(s) which resulted in the subject plant or cell (see, e.g., Green (1998) *Weed Technology* 12: 474-477; Green and Ulrich (1993) *Weed Science* 41: 508-516). In other embodiments, the null segregant can be used as a control, as they are genetically identical to HCEM485 with the exception of the insert DNA.

Generally, the effective amount of herbicide applied to the field is sufficient to selectively control the weeds without significantly affecting the crop. "Weed" as used herein refers to a plant which is not desirable in a particular area. Conversely, a "crop plant" as used herein refers to a plant which is desired in a particular area, such as, for example, a maize plant. Thus, in some embodiments, a weed is a non-crop plant or a non-crop species, while in some embodiments, a weed is a crop species which is sought to be eliminated from a particular area, such as, for example, an inferior and/or non-genetically modified maize plant in a field planted with maize event HCEM485, or a maize plant in a field planted with HCEM485.

As used herein, by "selectively controlled" it is intended that the majority of weeds in an area of cultivation are significantly damaged or killed, while if crop plants are also present in the field, the majority of the crop plants are not significantly damaged. Thus, a method is considered to selectively control weeds when at least 55%, 60%, 65%, 70%, 75%, 80%, 85%, 90%, 95%, or more of the weeds are significantly damaged or killed, while if crop plants are also present in the field, less than 45%, 40%, 35%, 30%, 25%, 20%, 15%, 10%, 5%, or 1% of the crop plants are significantly damaged or killed.

In specific embodiments, a glyphosate composition is applied to the maize HCEM485, wherein the effective concentration of the glyphosate composition would significantly damage an appropriate control plant.

As disclosed elsewhere herein, any effective amount of these herbicides can be applied and is readily known by one skilled in the art. In some embodiments of the invention, glyphosate is applied to an area of cultivation and/or to at least one plant in an area of cultivation at rates between 8 and 32 ounces of acid equivalent per acre, or at rates between 10, 12, 14, 16, 18, 20, 22, 24, 26, 28, and 30 ounces of acid equivalent per acre at the lower end of the range of application and between 12, 14, 16, 18, 20, 22, 24, 26, 28, 30, and 32 ounces of acid equivalent per acre at the higher end of the range of application (1 ounce=29.57 ml). In other embodiments, glyphosate is applied at least at 1, 5, 10, 20, 30, 40, 50, 60, 70, 80, 90 or greater ounce of active ingredient per hectare (1 ounce=29.57 ml). Additional ranges of the effective amounts of herbicides can be found, for example, in various publications from University Extension services. See, for example, Bernards et al. (2006) Guide for Weed Management in Nebraska (www.ianrpubs.url.edu/sendlt/ec130); Regher et al. (2005) Chemical Weed Control for Fields Crops, Pastures, Rangeland, and Noncropland, Kansas State University Agricultural Extension Station and Corporate Extension Service; Zollinger et al. (2006) North Dakota Weed Control Guide, North Dakota Extension Service, and the Iowa State University Extension at www.weeds.iastate.edu.

The herbicide is applied in any manner appropriate for the circumstances, whether prior to the plant emerging, or after the plant emerges. In one embodiment, methods are provided for coating seeds. The methods comprise coating a seed with an effective amount of an herbicide or a combination of herbicides (as disclosed elsewhere herein). The methods of the invention encompass the use of simultaneous and/or sequential applications of multiple classes of herbicides. In some embodiments, the methods of the invention involve treating a plant of the invention and/or an area of interest (e.g., a field or area of cultivation) and/or weed with just one herbicide or other chemical such as, for example, a sulfonylurea herbicide. The composition applied to the plants may include any other desirable ingredients, such as additional chemicals such as insecticides or other herbicides or the like, adjuvants, surfactants, or other desired component. Further, compositions may be provided at the same time or sequentially to application of the glyphosate herbicide, as noted, which can be any composition that is agronomically desirable, such as fertilizer, a second herbicide, an insecticide, or the like.

The following is provided by way of illustration and is not intended to be limiting to the scope of the invention.

Example 1

Glyphosate herbicide-tolerant maize line HCEM485 was produced by introducing a 6.0 kb maize genomic fragment containing a modified form of the endogenous maize EPSPS encoding gene. The sequence providing tolerance to glyphosate exposure is described at U.S. Pat. No. 7,045,684, incorporated herein by reference in its' entirety. The sequence is SEQ ID NO: 2. The 6.0 kb fragment includes an EPSPS 5' regulatory sequence (the sequence before nucleotide 1868), an EPSPS exons and introns sequence (from nucleotide 1868 to nucleotide 5146), and an EPSPS 3' regulatory sequence (the sequence after nucleotide 5146). The EPSPS coding sequence also encodes a putative chloroplast transit peptide (from nucleotide 1868 to nucleotide 2041). The two mutations introduced into the corn wild-type EPSPS gene are a cytosine to thymine substitution at nucleotide 2886, and a cytosine to thymine substitution at nucleotide 2897. The mutated gene (referred to as HCEM) encodes a mutant protein which is SEQ ID NO: 3 with the residue at position 164 changed from threonine in the wild-type to isoleucine (Thr to Ile) and at position 168 changed from proline to serine (Pro to Ser). The resulting mutated protein was glyphosate resistant.

The mutated nucleotide sequence of SEQ ID NO: 2 includes 2mEPSPS, that is, in this instance, the native corn EPSPS promoter, coding region (containing the two mutations), introns and 3' terminator region. FIG. 1 shows the plasmid map of pHCEM containing the 6.0 kb ClaI-EcoRV fragment cloned into pBlueScript vector. The positions of relevant restriction endonuclease sites and of probes used in Southern hybridization analyses are indicated with numbering relative to the plasmid DNA sequence. For DNA introduction, pHCEM was digested with ClaI and EcoRV, subjected to agarose gel electrophoresis (1 percent agarose), and the 6.0 kb band was excised and purified using Qiagen's Qiaquick gel extraction kit.

This was introduced into a corn plant as described in Example 4 of the '684 patent, incorporated herein by reference in its entirety, and resulted in event HCEM485 wherein the introduced DNA is located on chromosome 10. DNA introduction was via aerosol beam injector, which is a naked DNA delivery method. The purified maize DNA fragment was introduced into immature maize embryos derived from the elite inbred line Stine 963 by aerosol beam injection. Aerosol beam technology employs the jet expansion of an inert gas as it passes from a region of higher gas pressure to a region of lower gas pressure through a small orifice. The expanding gas accelerates aerosol droplets containing the molecules to be introduced into a cell or tissue. DNA carried in aerosol droplets of this small size penetrates cells only because of the speeds attained by the aerosol droplets. Speeds achieved by the aerosol beam method of the invention are supersonic and can reach 2,000 meters/second. In a preferred embodiment, the process includes (I) culturing a source of cells, (II) optionally, pretreating cells to yield tissue with increased capacity for uptake and integration by aerosol beam technology, (III) transforming said tissue with an exogenous nucleotide sequence by the aerosol beam method of the invention, (IV) optionally, identifying or selecting for transformed tissue, (V) optionally regenerating transgenic plants from the transformed cells or tissue, and (VI) optionally, producing progeny of said transgenic plants. This process is described in detail at Held et al., U.S. Pat. Nos. 6,809,232; 7,067,716; and 7,026,286, incorporated herein by reference in their entirety. After 5 days of culture on non-selective medium, embryos were transferred onto medium containing glyphosate (100 mg/l). After two 14-day passages, embryos were transferred onto medium containing successively greater glyphosate concentrations, up to 540 mg/1, and regeneration was carried out as previously described (See '684 patent)

Example 2

The introduced sequences in maize line HCEM485 are contained within a single genetic locus within the maize genome as demonstrated by Southern blot analysis and Mendelian inheritance studies. The modified maize EPSP synthase expressed in maize line HCEM485 is intact, of the expected molecular weight and there was no evidence of truncated forms of the enzyme.

Southern analysis of HCEM485 maize DNA was performed in order to estimate the number of sites of insertion of the introduced DNA. Two probes were used that together spanned the entire 6.0 kb maize DNA fragment introduced into HCEM485. These probes were designated:

a) A/C—obtained from a double digest of the pHCEM plasmid with ClaI and Acc65I (corresponding to positions 1-2346) (SEQ ID NO: 21); and b) A/E—obtained from a double digest of the pHCEM plasmid with Acc65I and EcoRV (corresponding to positions 2347-6010) (SEQ ID NO: 22) Probes (ca. 50 ng each) were labeled with 50 μCi of (α-32P)-dCTP (3000 Ci/mmol) using a random labeling system (Rediprime™ II, Amersham Piscataway, N.J.). Genomic DNA (7 μg) isolated from HCEM485 and control Stine 963 maize was digested (37° C., overnight) with HindIII and restriction fragments were separated by agarose gel electrophoresis followed by transfer onto Hybond N+ nylon membrane. Southern hybridizations were performed according to standard procedures.

Figure 2:
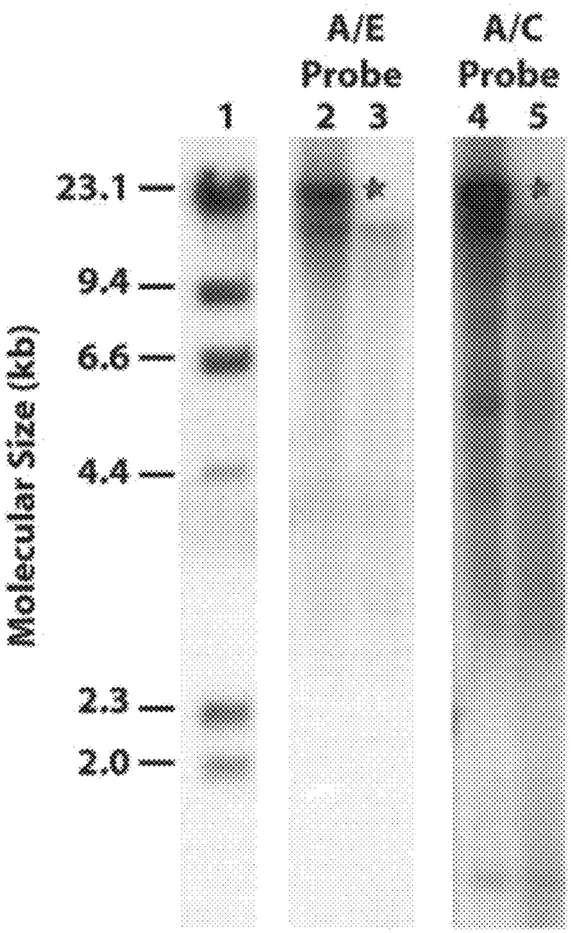
FIG. 2 shows a southern blot hybridization of HCEM with A/E and A/C probes.

Southern analysis of HCEM485 genomic DNA using both the A/C (FIG. 2, lane 4) and A/E (FIG. 2, lane 2) probes following HindIII digestion indicated the presence of a single >=23 kb hybridizing fragment that was unique to HCEM485 (i.e., not present in digests of control Stine 963 maize DNA). As there are no HindIII sites within the 6.0 kb maize DNA fragment introduced into HCEM485 and based on results from Southern analyses using other restriction endonucleases, it is postulated that multiple copies of the 6.0 kb fragment, approximately 4, were inserted at a single site within the maize genome.

Example 3

The Line 963 HCEM485 plant was selfed over two generations and crossed with line 9289, yielding $F_1$ hybrids hemizygous for the insert. A single plant from this cross was crossed with line 9032, yielding $F_1$ populations expected to segregate 1:1 for the glyphosate tolerance trait. The $F_2$ generation was produced by selfing a single trait-positive plant from the preceding $F_1$ generation. Progeny $F_2$ plants should segregate 3:1 for the glyphosate-tolerance trait.

Segregation analysis was conducted on $F_1$ and $F_2$ segregating plant populations derived from maize line HCEM485 as described by screening for glyphosate tolerance. Progeny plants of each generation were grown in the greenhouse and treated with 2.5× the recommended field application rate of glyphosate at approximately the V4 stage of plant development and visually scored for herbicide susceptibility. Numbers of trait positive and trait negative plants from each generation are shown in Table 1.

TABLE 3

Observed vs. expected segregants for F1 hybrid and F2 selfed generations derived from HCEM485 maize

| | (9289xHCEM485)9032 F1 | | (9289xHCEM485)9032 S1F2 | |
|---|---|---|---|---|
| | Observed | Expected | Observed | Expected |
| Trait Positive[1] | 129 | 124.5 | 107 | 108 |
| Trait Negative | 120 | 124.5 | 37 | 36 |
| Total | 249 | 249 | 144 | 144 |
| Expected Segregation Ratio | 1:1 | | 3:1 | |
| Observed Segregation Ratio | 1.036:0.964 | | 2.972:1.028 | |
| $\chi^2$ | 0.930 | | 0.624 | |

[1]Differentiation of trait positive and trait negative plants was based on tolerance to glyphosate. Plants were sprayed at the V4 stage of development with 2.5X the normal rate of glyphosate application (1X = 32 oz/acre).

[2]For significance at the 95% confidence level ($p < 0.05$), the Chi square value should be >= 3.841. Chi square values <3.841 indicate that the null hypothesis (i.e., observed and expected segregation ratios are not significantly different) should not be rejected at the 95% confidence level.

The data in Table 1 were used to assess the goodness-of-fit of the observed ratios to the expected ratios using Chi Square analysis with Yates correction factor.

$$\chi^2=\Sigma[\text{Observed-expected}-0.5]2/\text{expected}$$

This analysis tested the hypothesis that the introduced trait segregated as a single locus in a Mendelian fashion. The critical value to reject the hypothesis at the 5% level is 3.84. Since the Chi squared value was less than 3.84 (Table 1), the hypothesis that the genetic trait behaved in a Mendelian fashion was accepted.

Example 4

In order to confirm the absence of any plasmid backbone sequences within the HCEM485 genome, samples of genomic DNA from plants of the $T_2$ generation described in Example 3. The samples were digested with HindIII followed by Southern hybridization using the C/E probe, which was complementary to the plasmid backbone sequences in vector pHCEM. There were no detectable hybridization signals from samples derived from maize line HCEM485, consistent with the lack of incorporation of any vector backbone derived sequences in the maize genome.

Example 5

A Western blot analysis was conducted with a monoclonal antibody specific to 2mEPSPS to assess the integrity of the expressed protein in maize line HCEM485. The Western blot analysis demonstrated that the 2mEPSPS protein expressed in leaf and seed tissues from line HCEM485 was intact and was of the expected size corresponding to the EPSPS protein. There were no cross-reacting species detected in control samples of parental Stine 963 maize, indicating that the monoclonal antibody used for detection was specific for the modified form of the maize EPSP synthase. The monoclonal antibody used is that described at U.S. Pat. No. 7,807,791 which is incorporated herein by reference in its entirety. The antibody is useful in identifying the presence of the 2mEPSPS gene.

Example 6

Figure 3:
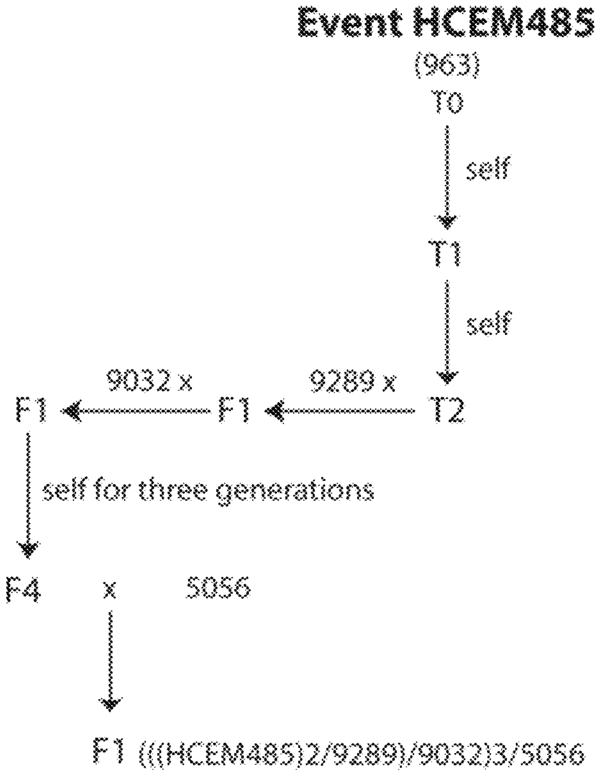
FIG. 3 is a diagram of the process for producing plants for agronomic and phenotypic comparisons.

Agronomic and phenotypic characteristics of an HCEM485 maize hybrid and three control hybrids were evaluated in a series of field trials across 15 United States Corn Belt locations. These trials used the following comparisons:

HCEM485 hybrid (((HCEM485)2/9289/9032)3/5056) [trait positive] (see FIG. 3)
Control hybrid 9289×5056 [trait negative]
Control hybrid 9032×5056 [trait negative]
Control hybrid 963×5056 [trait negative]

Up to 17 separate agronomic characteristics were assessed at each location, but not all traits were assessed at all locations. These agronomic traits covered a broad range of characteristics encompassing the entire life cycle of the maize plant and included data assessing germination and seedling emergence, growth habit, vegetative vigor, days to pollen shed, days to maturity, and yield parameters Parameters used to evaluate yield and grain characteristics included: YGSMN (grain yield); HAVPN (plant population at harvest); DROPP (percent dropped ears); TWSMN (grain test weight); and GMSTP (grain moisture percent). Among the varieties suitable for statistical analysis, there were no significant differences in average yield, plant population at harvest, grain moisture, or grain test weight between HCEM485 and control hybrids (Table 8). For both yield and plant population at harvest, there were significant genotype x location interactions. Although not subject to statistical analysis, there were no remarkable differences in percent dropped ears between HCEM485 and control genotypes (Table 2).

TABLE 2

Comparison of yield and grain characteristics of HCEM485 and control hybrids

| | YGSMN[a] (bu/acre) | HAVPN (plants/acre) | DROPP (%) | GMSTP (%) | TWSMN (lb/bu) |
|---|---|---|---|---|---|
| HCEM485 hybrid | 115.4 ± 51.2 | 14976 ± 3410 | 0.06 | 18.8 ± 7.7 | 55.2 ± 1.9 |
| Control hybrids | 113.9 ± 50.7 | 14888 ± 3622 | 0.04 | 18.3 ± 7.1 | 55.2 ± 2.3 |
| Mean Difference | 1.5 | 88 | 0.02 | 0.5 | 0.1 |
| F-test genotype | 0.621 | 0.818 | | 0.051 | 0.731 |
| F-test genotype × location | 0.003** | 0.040** | | 0.463 | 0.431 |
| N[b] | 13 | 14 | 14 | 13 | 13 |

**= indicates that the effect of genotype was not consistent across all locations, in which case the comparison of genotype averaged across locations is questionable.
[a]YGSMN = grain yield; HAVPN = final stand count at harvest; DROPP = percent dropped ears; GMSTP = grain moisture percent; TWSMN = grain test weight. Mean values are shown. For YGSMN, HAVPN and GMSTP, the mean standard deviation is indicated.
[b]N = number of locations with data.

In summary, the agronomic characteristics chosen for comparison were those typically observed by professional maize breeders and agronomists and represented a broad range of characteristics throughout the development of the maize plant. Results of these trials suggest that there were no biologically significant unintended effects on plant growth habit and general morphology, vegetative vigor, flowering and pollination, grain yield, grain test weight, or disease susceptibility as a result of the genetic modification introduced into maize line HCEM485.

Example 7

Flanking sequence of the integrated DNA fragment called HCEM in event HCEM485 was sought for the purpose of generating event specific PCR based assays. The HCEM DNA fragment contains a double mutant epsps gene (2mepsps) including the promoter region, introns, exons, and 3' terminator region (U.S. Pat. No. 7,045,684). HCEM485 DNA and control DNA from Inbred 963 was obtained from leaves of corn plants using ‘Plant DNeasy Kit’ from Qiagen. Ample concentrated DNA was obtained in a highly pure form from both the controls and the HCEM485 plants using the Qiagen protocol. Primers were designed for amplification of DNA using segments of known sequence from the HCEM DNA fragment. Primers designed for the 3' end of HCEM were named in the 300's. The complete sequence of the relevant primer (302) is listed below:

```
                                        (SEQ ID NO: 5)
    Primer 302: ATGTTACTATGGTGCCTTCTTATCC
```

Figure 5:
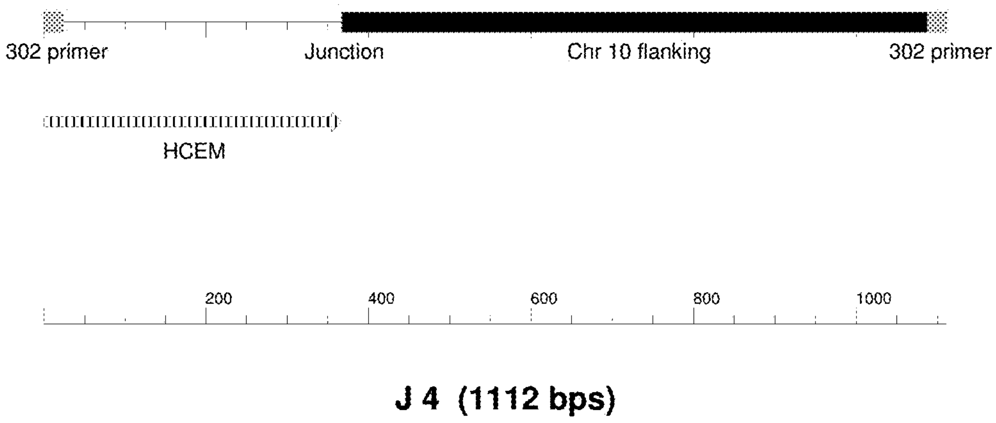
FIG. 5 is a diagram of the plasmid J4 showing genetic elements including the location of Primer 302 and its complementary sequence, the 3' HCEM region and flanking region of chromosome 10.

In addition, a random 9-mer was used in an attempt to anchor the reaction in the unknown flanking sequence. A PCR process was used to amplify the desired segment of DNA, which produced a clear band when the HCEM485-exhibitor DNA sample was run on a gel. No corresponding band resulted from the control DNA under identical conditions. The PCR process was TAIL PCR (Thermal Asymmetric Interlaced Polymerase Chain Reaction), and used two separate steps to isolate flanking sequence. The PCR proceeded as follows:

First Stage PCR:
25 ul Qiagen Taq PCR Master Mix
23.5 ul $H_2O$
1 ul Primer 302 at a concentration of 1 ug/ul $H_2O$
1 ul DNA (485) at a concentration of 1 ug/ul $H_2O$
First Stage Cycle Parameters:
Cycle 1:
2 minutes at 95° Celsius
1 Repetition
Cycle 2:
25 seconds at 95° Celsius
35 seconds at 60° Celsius
2 minutes and 30 seconds at 70° Celsius
35 repetitions
Second Stage PCR:
25 ul Qiagen Taq PCR Master Mix
20 ul $H_2O$
10 ul 485 (302) PCR product
1 ul random 9-mer at a concentration of 1 ug/ul $H_2O$
1 ul primer 302 at a concentration of 1 ug/ul $H_2O$
Second Stage Cycle Parameters:
Cycle 1:
2 minutes at 95° Celsius
1 Repetition
Cycle 2:
25 seconds at 95° Celsius
35 seconds at 45° Celsius
1 minute 45 seconds at 70° Celsius
35 Repetitions The resultant reaction mixtures were run on a gel with a DNA marker and a band of about 1,100 base pairs was identified for the HCEM485 sample. No band of that size was identified for the 963 control. The DNA band was extracted from the gel using "Gel Extraction Kit" protocol from Qiagen. The DNA was cloned into "pGEM T-Easy" plasmid (Promega) according to manufacturer instructions. The resulting plasmid was isolated using a Qiagen "Maxi-Prep Procedure" and called J4. The sample was sent to the ISU DNA Facility for nucleotide sequence analysis. The sequence illustrated in FIG. 4 was obtained. The J4 fragment is 1112 base pairs in length and is flanked by primer 302 which indicates the reaction was anchored on both ends by primer 302. Primer 302 (SEQ ID NO: 5) is shown underlined at the beginning of the sequence. The region complementary to Primer 302 is underlined at the end of the sequence in FIG. 4 (SEQ ID NO: 6). The first 367 nucleotides have 100% homology to the 3' sequence of the HCEM fragment (SEQ ID NO: 7). The junction at positions 367/368 is italicized and bolded in FIG. 1. The rest of the J4 sequence (positions 368-1112, SEQ ID NO: 8) was blasted against the entire corn genome (www.maizesequence.org/blast). This revealed 100% homology over the length of 725 continuous base pairs (positions 368-1092, SEQ ID NO: 9) to a section of the tenth chromosome, allowing us to conclude that the HCEM fragment was inserted in the tenth chromosome. Downstream of position 1092 (positions 1093-1112) of SEQ ID NO: 4 the homology is much less to the corn genome continuous to the region of 100% homology (non-homology is displayed by small letters in FIG. 1). However, the homology was apparently enough to allow priming with the 302 primer at the low annealing temperature of 45° C. FIG. 5 is a graphic representation of location of the regions in the plasmid.

Primers were designed using the identified flanking region. The sequence of the relevant primer (506) is listed below and its compliment appears in bold font in Seq. 1:

```
                                        (SEQ ID NO: 10)
    Primer 506: CGCCCAGTAGGTACACTAAG
```

This primer was used in combination with primer 302 in a PCR procedure to verify difference between the control DNA Inbred 963 and the HCEM485 exhibitor. The reaction was set up as follows:

PCR:
12.5 ul Qiagen Taq PCR Master Mix
11 ul $H_2O$
0.5 ul Primer 302 at a concentration of 1 ug/ul $H_2O$
0.5 ul Primer 506 at a concentration of 1 ug/ul $H_2O$
1 ul DNA (HCEM485 or Inbred 963) at a concentration of 1 ug/ul $H_2O$
Cycle Parameters:
Cycle 1:
2 minutes at 90° Celsius
1 Repetition
Cycle 2:
25 seconds at 90° Celsius
35 seconds at 45° Celsius
2 minutes 30 seconds at 72° Celsius
35 Repetitions This reaction yielded a band of about 1,000 base pairs when performed with template DNA from HCEM485, while no such band resulted from the reaction containing DNA from Inbred 963. Due to the expected size and the fact that it is unique to HCEM485, we conclude that the reaction is event-specific.

Example 8

The presence of the HCEM485 Maize transformation event in genomic DNA extracted from seed tissue was confirmed using a TaqMan® assay. Specific detection of the HCEM485 event used PCR amplification of the region that spans a junction site of the HCEM485 insert and genomic flanking sequences (see FIGS. 4 and 5). Amplification was achieved using two specific primers which amplify a 121 bp DNA fragment (Table 5). Amplification was measured with a target-specific MGB probe containing the FAM reporter. The protocol below outlines the reaction reagents, the oligonucleotide primers and probes, and the thermocycling conditions used to perform the reaction.

Preparation of DNA Template

DNA was extracted from ground maize seed using the Plant DNeasy Kit from Qiagen. DNA was quantified and diluted to a final concentration of 25 ng/ul with DNase-free water. It is recommended to use control DNA that was extracted and normalized using the same method as the samples to be analyzed. The controls for this analysis included positive control from HCEM485 transgenic maize, negative control from non-transgenic maize and negative control that contains no template DNA.

Polymerase Chain Reaction

A. Prepare Reaction Mixture

The procedure involved determining the number of reactions to be performed, including controls and prepare a master mix consisting of all components of the reaction, except the template, to supply all reactions plus 10% excess.

TABLE 3

| PCR reagent | Final Conc. | Volume per reaction | Final Volume |
|---|---|---|---|
| ddH2O | | .31 | |
| TaqMan Gene Exp PCR MM (2X) | 1X | 10 | |
| HCEM485 Forward Primer SB060 (25 uM) | 0.9 uM | 0.72 | |
| HCEM485 Reverse Primer SB061 (25 uM) | 0.9 uM | 0.72 | |
| HCEM485 Probe SBTM021 (20 uM) | 0.25 uM | 0.25 | |
| Total Volume | | 12 | |

12 ul of PCR reaction mix was aliquoted to each PCR tube/well. 8 ul of DNA (25 ng/ul) of each sample and control was added to individual PCR tube/well and mixed well by pipetting up and down. The reaction tube/plate was sealed and centrifuged at low speed to spin down the reaction mixture.

B. PCR Amplification

The following cycling parameters were used with the Applied Biosystems Step-One Plus Real-Time PCR System.

TABLE 4

| Temperature | Time | Cycle No. | Data Collection |
|---|---|---|---|
| 60° C. | 30 Sec | 1 | Yes |
| 50° C. | 2 Min | 1 | No |
| 95° C. | 10 Min | 1 | No |
| 95° C. | 15 Sec | 40 | Yes |
| 60° C. | 1 Min | | |
| 60° C. | 30 Sec | 1 | Yes |

PCR primers, HPLC purified (Integrated DNA Technologies)

PCR probe (Applied Bio systems)

Equipment

Thermocycler: Applied Biosystems Step-One Plus Real-Time PCR System

The PCR assay was optimized and validated for use in 96-well format using an Applied Biosystems Step-One Plus Real-Time PCR System. Other systems may be used, but thermal cycling conditions must be verified. Event specificity of the assay was tested against DNA extracted from eight different genetic backgrounds, one of which was a HCEM485 line. The HCEM485 line resulted in an amplification signal while no signal was detected in any negative control sample within 50 amplification cycles.

Sensitivity of the assay was tested against DNA extracted from pooled seed samples with varying amounts of HCEM485 presence. Seed samples consisted of HCEM485 seed pooled with non-transgenic conventional maize seed at ratios of 10:0, 1:10, 1:25, 1:50, and 1:100 (HCEM485:non-transgenic seed). The assay was shown to reproducibly detect HCEM485 in all seed combinations tested. Performance was verified using positive and negative blind samples. HCEM485 was detected in all positive controls and blind samples containing HCEM485 while negative controls and negative blind samples did not produce a signal.

LIST OF SEQUENCES

SEQ ID NO: 1 genomic EPSPS wild-type corn fragment

SEQ ID NO: 2 mutated corn EPSPS nucleotide sequence HCEM

SEQ ID NO: 3 amino acid sequence encoded by SEQ ID NO: 2

SEQ ID NO: 4 amplified nucleotide sequence of the flanking region of the 3' sequence of HCEM and flanking region of chromosome 10.

SEQ ID NO: 5 302 primer

SEQ ID NO: 6 sequence complement to 302 primer

SEQ ID NO: 7 first 367 bp of SEQ ID NO: 4

SEQ ID NO: 8 bp 368-1112 of sequence 4

SEQ ID NO: 9 bp 368-1092 of sequence 4

SEQ ID NO: 10 506 primer

SEQ ID NO: 11 sequence complement to 506 primer

SEQ ID NO; 12 junction region—last 10 bp of HCEM flanking region and first 10 of chromosome 10 flanking region

TABLE 5

| PCR primers and probes | | |
|---|---|---|
| Name | Description | Sequence 5' to 3' |
| SB060 | Forward Primer targeted to the T-DNA sequence | CATTGAAAGGCATCTTAGCAATGTCTAAA (SEQ ID NO: 18) |
| SB061 | Reverse Primer targeted to the genomic flanking sequence | CCACCCAGTCTCACTCAATCTAATACTATAT (SEQ ID NO: 19) |
| SBTM021 | 6-FAM MGB probe targeted to the T-DNA/ flanking sequence junction | CCAAGCCCTATAAGACATCAA (SEQ ID NO: 20) |

PCR reagents

2×TaqMan® Gene Expression Master Mix (Applied Biosystems)

SEQ ID NO: 13 junction region—last 20 bp of HCEM flanking region and first 20 of chromosome 10 flanking region SEQ ID NO: 14 junction region—last 30 bp of HCEM flanking region and first 30 bp of chromosome 10 flanking region.

SEQ ID NO: 15 junction region—entire HCEM flanking region, bases 1-367 of SEQ ID NO: 4, and chromosome 10 flanking region by 368-1092 of sequence 4

SEQ ID NO: 16 junction region—all of HCEM (SEQ ID NO: 2) and all of chromosome 10 flanking region by 368-1112 (SEQ ID NO: 8)

SEQ ID NO: 17 junction region—HCEM (SEQ ID NO: 2) and bp368-1092 of chromosome 10 flanking sequence (SEQ ID NO: 9)

SEQ ID NO: 18 Primer SB060

SEQ ID NO: 19 Primer SB061

SEQ ID NO: 20 TaqMan® 6-FAM MGB probe SBTM021

SEQ ID NO 21 Probe A/C

SEQ ID NO: 22 Probe A/E

What is claimed is:

1. A method of identifying event HCEM485 in a biological sample, said method comprising detecting a DNA molecule comprising at least one HCEM485 junction sequence in a biological sample with a specific probe or at least one specific primer which binds or amplifies a DNA molecule comprising said at least one HCEM485 junction sequence, reference seed comprising said HCEM485 event having been deposited under ATCC accession number PTA-12014.

2. The method of claim 1, wherein said DNA molecule detected comprises a junction sequence that is within SEQ ID NO: 4 or the full complement of SEQ ID NO: 4.

3. The method of claim 1, wherein said DNA molecule comprises a junction sequence selected from the group consisting of 4, 12, 13, 14, 15, 16 and 17.

4. The method of claim 1, wherein said DNA molecule is detected by amplification of a nucleic acid molecule using a primer selected from the group consisting of SEQ ID NO: 5, 6, 10, 11, 18 and 19 or the full length complement thereof.

5. The method of claim 1, wherein said DNA molecule is detected by amplification using a primer pair comprising SEQ ID NO: 5 and 10 or SEQ ID NO: 18 and 19.

6. The method of claim 1, wherein said DNA molecule is detected by a probe selected from the group consisting of SEQ ID NO: 21 and 22.

7. A kit for identifying the presence of event HCEM485 in a biological sample, said kit comprising a specific probe that binds at least the HCEM485 junction sequences or at least one specific primer that comprises at least the HCEM485 junction sequences, reference seed comprising said event having been deposited under ATCC accession number PTA-12014.

8. The kit of claim 7, wherein said junction sequence comprises a polynucleotide selected from the group consisting of SEQ ID NO: 4, 12, 13, 14, 15, 16 and 17.

9. The kit of claim 7, wherein said probe is selected from the group consisting of SEQ ID NO: 21 and 22.

10. An isolated polynucleotide comprising SEQ ID NO: 4, 12, 13, 14, 15, 16 and 17.

* * * * *

UNITED STATES PATENT AND TRADEMARK OFFICE

CERTIFICATE OF CORRECTION

PATENT NO. : 9,487,834 B2
APPLICATION NO. : 14/256525
DATED : November 8, 2016
INVENTOR(S) : Bruce Held et al.

It is certified that error appears in the above-identified patent and that said Letters Patent is hereby corrected as shown below:

On the Title Page

(73) Assignee should read:
"Stine Seed Farm, Inc."

Signed and Sealed this
Thirtieth Day of May, 2017

Michelle K. Lee

Michelle K. Lee
*Director of the United States Patent and Trademark Office*